United States Patent
Song et al.

(10) Patent No.: US 9,840,742 B2
(45) Date of Patent: Dec. 12, 2017

(54) DETECTION OF HEPATITIS B VIRUS (HBV) DNA AND METHYLATED HBV DNA IN URINE OF PATIENTS WITH HBV-ASSOCIATED HEPATOCELLULAR CARCINOMA

(71) Applicant: JBS Science Inc., Doylestown, PA (US)

(72) Inventors: Wei Song, Audubon, PA (US); Surbhi Jain, Doylestown, PA (US); Batbold Boldbaatar, Coastesville, PA (US); Sitong Chen, Audubon, PA (US)

(73) Assignee: JBS SCIENCE INC., Doylestown, PA (US)

( * ) Notice: Subject to any disclaimer, the term of this patent is extended or adjusted under 35 U.S.C. 154(b) by 0 days.

(21) Appl. No.: 14/741,442

(22) Filed: Jun. 16, 2015

(65) Prior Publication Data

US 2015/0361505 A1    Dec. 17, 2015

Related U.S. Application Data

(60) Provisional application No. 62/012,618, filed on Jun. 16, 2014.

(51) Int. Cl.
    *C12Q 1/68* (2006.01)
    *C12Q 1/70* (2006.01)

(52) U.S. Cl.
    CPC ........... *C12Q 1/6886* (2013.01); *C12Q 1/706* (2013.01); *C12Q 2600/154* (2013.01)

(58) Field of Classification Search
    CPC ........ C12C 2600/154; C12C 2523/125; G01N 33/6812; G01N 33/6893
    See application file for complete search history.

(56) References Cited

U.S. PATENT DOCUMENTS

| | | | | |
|---|---|---|---|---|
| 9,598,735 | B2 * | 3/2017 | Song | C12Q 1/6886 |
| 2011/0256538 | A1 * | 10/2011 | Su | C12Q 1/6886 435/6.11 |
| 2014/0155279 | A1 * | 6/2014 | Song | C12Q 1/6886 506/7 |

OTHER PUBLICATIONS

Yang et al. American Journal of Pathology, 2003, vol. 163, No. 3, pp. 1101-1107.*
Hernandez et al. PLoS one, 2010, vol. 5, Issue 3, pp. 1-5.*

* cited by examiner

*Primary Examiner* — Bao Li
(74) *Attorney, Agent, or Firm* — DLA Piper LLP (US)

(57) ABSTRACT

This application relates to a DNA marker for HBV-HCC detection and the methods, kits for quantitatively measuring the amount of HBV DNA and bisulfite treated HBV DNA, and methylated HBV DNA, and the aberrant methylation of the HBV genome for the used in the chronic HBV infected populations. Detection of the presence or absence of HCC, with elevated methylation levels in the one or more regions of DNA of the mammals as compared to the level of methylation in the one or more regions of DNA in the one or more control body fluids or tissues indicating the presence of the cancer, and the absence of elevated methylation levels indicating the absence of HCC.

2 Claims, 29 Drawing Sheets

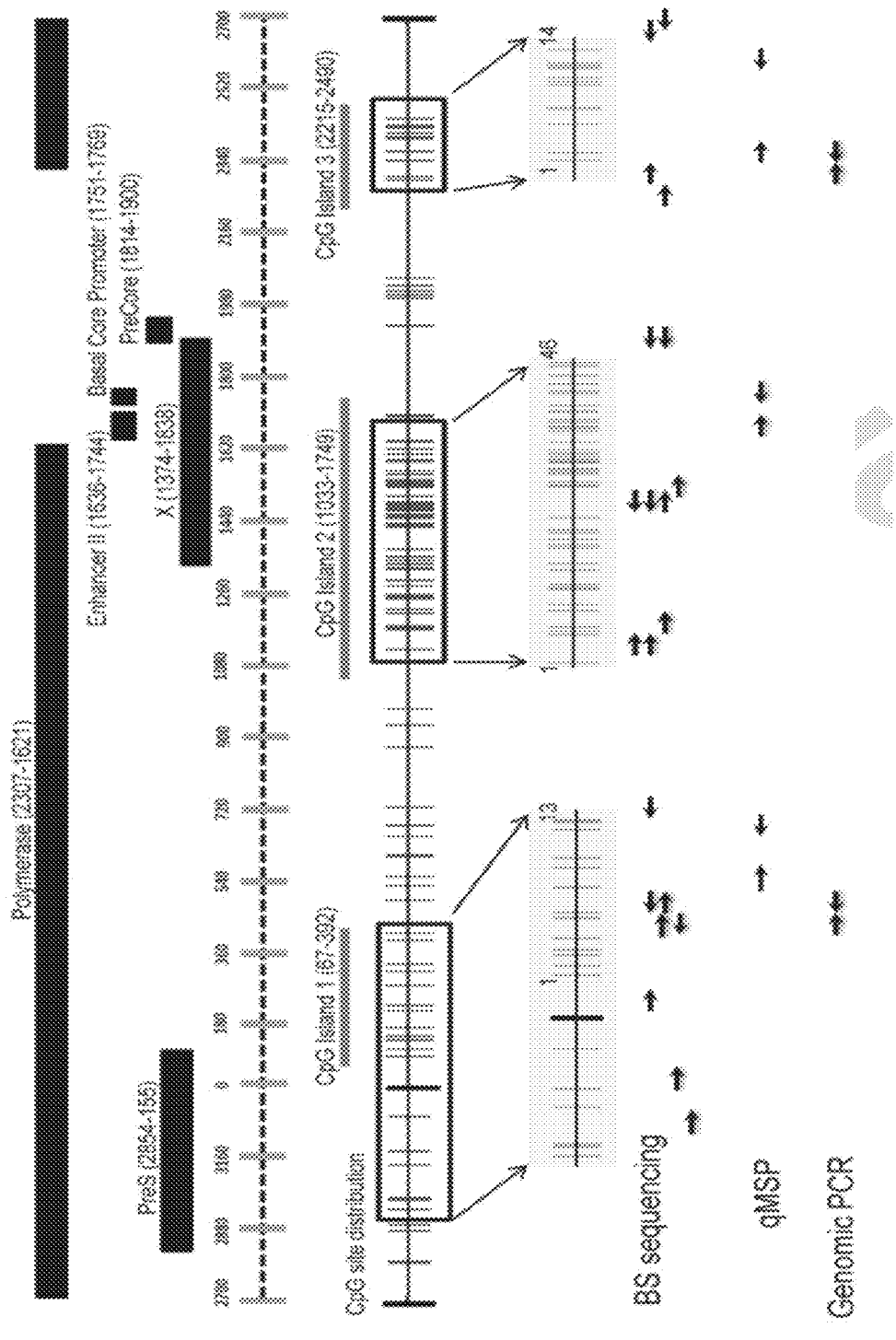
FIGURE 1. Diagram of the HBV genome indicating the location of the three CpG islands, CpG site distribution, and the primers for PCR assays used in this invention.

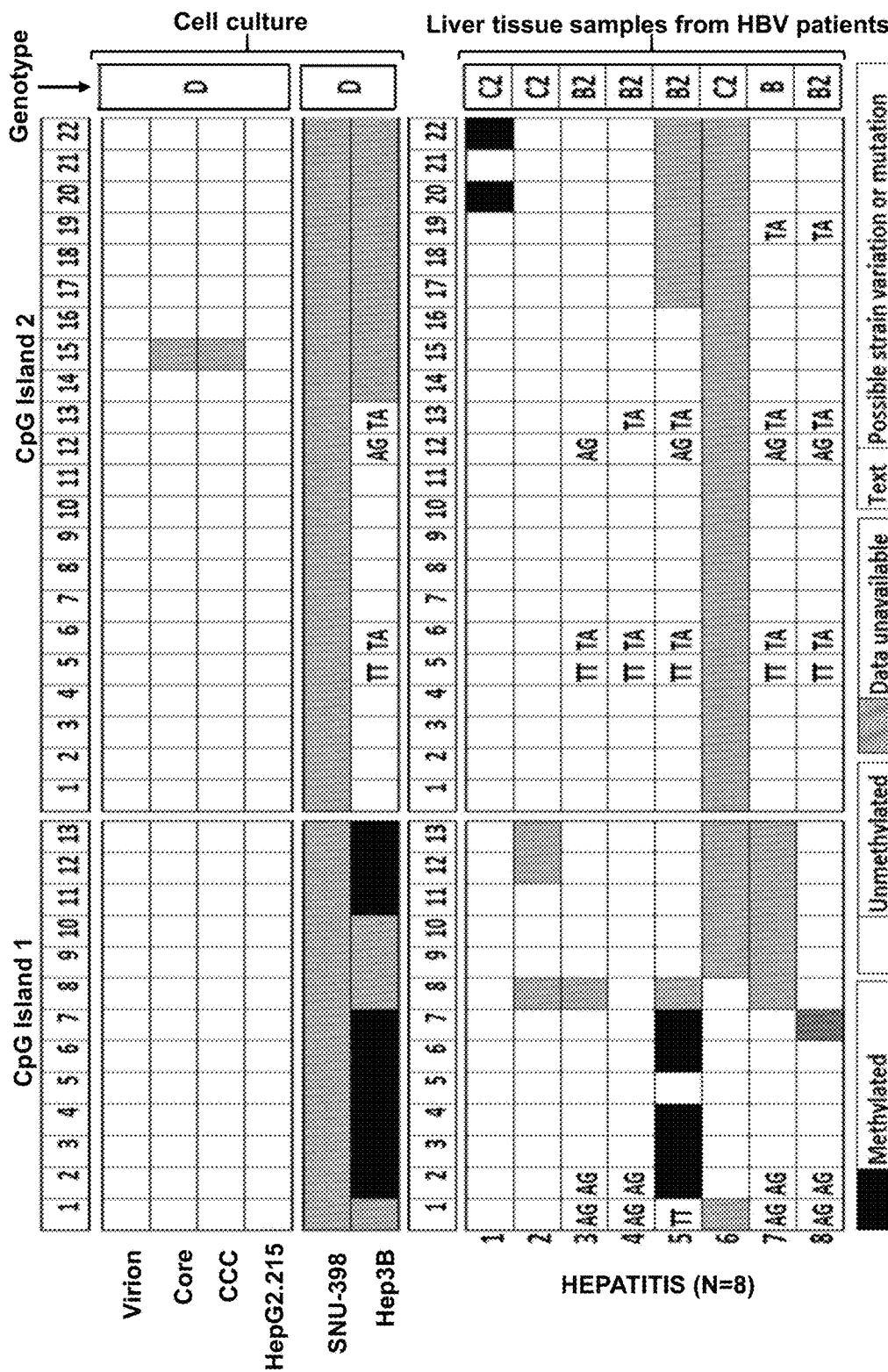
FIGURE 2. Methylation profile of the HBV genome by bisulfite sequencing.

FIGURE 3. Quantitative analysis of HBV DNA methylation in infected diseased livers.

FIGURE 4. Comparison of HBV and host gene methylation in HBV-HCC.

Figure 6

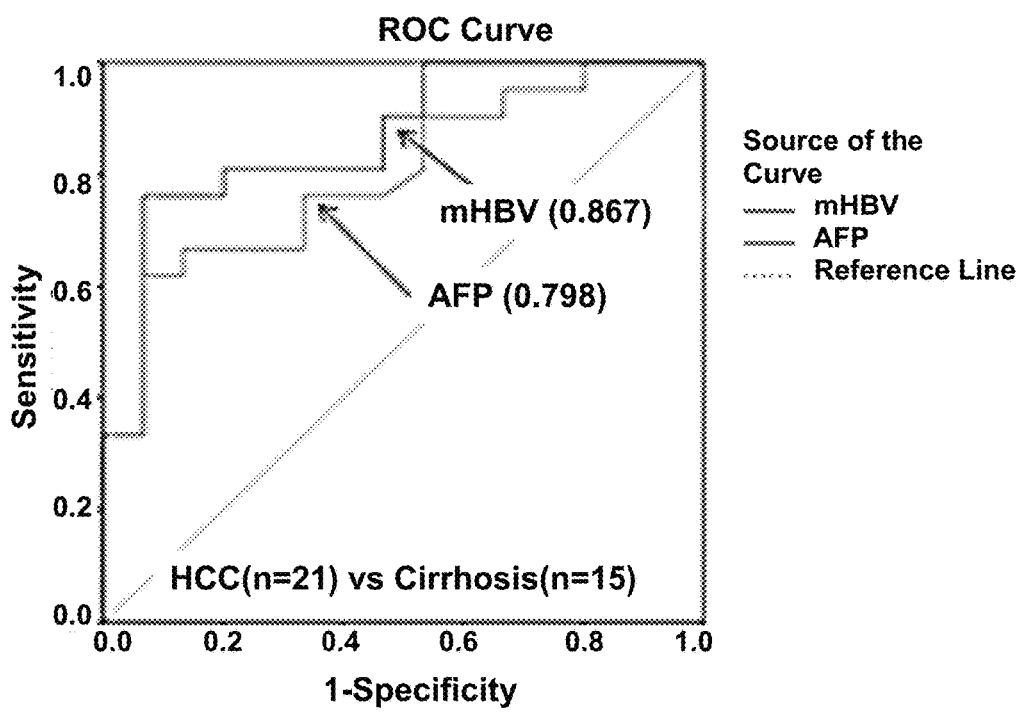

Area Under the Curve

| Test Result Variable(s) | Area | Std. Error[a] | Asymptotic Sig[b] | Asymptotic 95% Confidence Interval | |
|---|---|---|---|---|---|
| | | | | Lower Bound | Upper Bound |
| mHBV | .867 | .061 | .000 | .747 | .987 |
| AFP | .798 | .073 | .003 | .654 | .942 |

The test result variable(s): AFP has at least one tie between the positive actual state group and the negative actual state group. Statistics maybe biased.
  a. Under the nonparametric assumption
  b. Null hypothesis: true area = 0.5

Sensitivity of the HBV-MSP short amplicon assay up to 10 copies of HBV genome.

DETECTION OF HEPATITIS B VIRUS (HBV) DNA AND METHYLATED HBV DNA IN URINE OF PATIENTS WITH HBV-ASSOCIATED HEPATOCELLULAR CARCINOMA

CROSS-REFERENCE TO RELATED APPLICATIONS

The present application claims priority to U.S. Provisional Patent Application No. 62/012,618, filed Jun. 16, 2014, the contents of which are hereby incorporated by reference in its entirety.

GOVERNMENT FUNDING

This invention was (made with government support under 2R44CA165312-02, awarded by the National Cancer Institute. The government has certain rights in the invention.

REFERENCE TO SEQUENCE LISTING SUBMITTED ELECTRONICALLY

The content of the electronically submitted sequence listing, file name JBS0527720010.txt, size 8,560 bytes; and date of creation Aug. 21, 2015, filed herewith, is incorporated herein by reference in its entirety.

TECHNICAL FIELD

This invention relates to a method for detecting and quantitatively measuring hepatitis B virus (HBV) DNA, and its modifications including DNA methylation, and the modification in nucleic acid sequences associated with cancer using samples from tissue and biological fluid (blood or urine) of patients with chronic HBV infection.

BACKGROUND

Cancer is a disease of the genome. Identification of the genetic and epigenetic changes, such as aberrant DNA mutations and modifications underlying the development of carcinogenesis should provide unambiguous detection of cancer. These molecular changes, in concert with the genetic makeup of a patient, determine the clinical phenotype of the tumor, its response to a given treatment, and the patient's prognosis.

Hepatocellular carcinoma (HCC) is the most frequent cancer in certain parts of the world, and the fifth most cancer common worldwide. Increased incidence of HCC is associated with infections of hepatitis B virus and hepatitis C virus (El-Serag & Mason, 1999). Surgical resection is often curative if the disease is localized and diagnosis occurs early (Klintmalm, 1998). However, diagnosis of HCC is often late, resulting in extensive liver impairment associates with a poor prognosis, often due to late diagnosis. Late diagnosis of HCC is due to limited indicators. For example, among patients with underlying cirrhotic disease, a progressive increase in alpha-fetoprotein (AFP) and/or in alkaline phosphatase or a rapid deterioration of hepatic function may be the only clue to the presence of cancer.

Despite the availability of a preventative vaccine, chronic HBV infection remains a global health issue affecting more than 3500 million cases of HBV-related HCC (HBV-HCC). The HBV genome has 2-3 typical CpG islands depending on the genotype (Vivekanandan, Thomas, & Torbenson, 2008; Y. Zhang et al., 2013). Interestingly, these CpG islands are located at strategic locations in the regulatory elements of the HBV genome. For example, CpG island 1 is located in the first exon start site for the S (surface antigen) gene, and CpG islands 2 and 3 cover the enhancer II and the promoter of pregenomic RNA and the first exon start site of the polymerase gene, respectively (Moolla, Kew, & Arbuthnot, 2002; Vivekanandan et al., 2008). Although the virion DNA was found to be mostly unmethylated in both tissue culture and patient serum (Kaur et al., 2010; Vivekanandan et al., 2008), DNA methylation of the intranuclear HBV genome has been associated with repression of gene transcription in cultures (Guo, Li, Mu, Zhang, & Yan, 2009; Kim et al., 2011; Zhang, Hou, & Lu, 2013). Despite the difficulty of dissecting HBV DNA in diseased tissues, higher levels of methylation of CpG islands were found in HCC tissues compared to hepatitis and cirrhosis tissues, thus, methylation of HBV DNA has been associated with hepatocarcinogenesis.

Current methods of detection of HBV DNA genome and methylated HBV DNA are either not available or insensitive for fragmented DNA such as formalin fixed paraffin embedded (FFPE) tissues, DNA isolated from body fluids, merely qualitative. There remains a need for assays to quantitatively measure for the HBV DNA and its modifications (methylation) that can be used to monitor for the presence of HBV DNA and its modifications that are related to HCC and to screen for HCC so that HCC can be detected early and administered early.

SUMMARY

One aspect of the present application is a method of detecting the presence or absence of hepatitis B virus (HBV)-associated hepatocellular carcinoma (HCC) in a mammal, comprising:
(i) isolating DNA from one or more body fluids or tissues from said mammal;
(ii) quantifying HBV DNA by real-time quantitative PCR assays and the methylation level of one or more regions of HBV DNA with a quantitative methylation assay;
(iii) comparing the level of methylation of the one or more regions of DNA with the level of methylation of the one or more regions of DNA in one or more control body fluids or tissues from mammals known not to have HCC; and
(iv) detecting the presence or absence of HCC, with elevated methylation levels in the one or more regions of DNA of the mammals as compared to the level of methylation in the one or more regions of DNA in the one or more control body fluids or tissues indicating the presence of the cancer, and the absence of elevated methylation levels indicating the absence of HCC.

In one embodiment, the body fluids are from circulation body fluids.

In another embodiment, the body fluids is selected from the group consisting of: (i) urine; (ii) blood; (iii) serum; (iv) plasma; and (v) salvia.

In yet another embodiment, the mammal is a human being.

In yet another embodiment, the one or more regions of DNA are the CpG islands 1, 2 or 3 of the HBV genome, and the aberrant methylation of the CpG islands 1, 2 or 3, as determined by qMSP, indicates HCC.

In one embodiment, the quantitative methylation assay comprises a quantitative bisulfite specific PCR (BSP) to quantify bisulfite-treated HBV DNA and a quantitative methylation specific PCR (MSP).

In another embodiment, the one or more regions of HBV DNA is CpG island 1, wherein the forward primer, reverse primer and the probe of the BSP are nucleotide sequences of SEQ ID No. 1, SEQ ID No. 2, SEQ No. 3, respectively, wherein the forward primer, reverse primer and the probe of the MSP are nucleotide sequences of SEQ ID No. 4, SEQ ID No. 5, SEQ No. 6, respectively, wherein the HBV DNA is quantified by real-time quantitative PCR using a forward primer, a reverse primer and a probe, wherein the forward primer, the reverse primer and the probe of the real-time quantitative PCR are nucleotide sequences of SEQ ID No. 25, SEQ ID No. 26 and SEQ ID No. 27, respectively.

In another embodiment, the one or more regions of HBV DNA is CpG island 2, wherein the forward primer, reverse primer and the probe of the BSP are nucleotide sequences of SEQ ID No. 7, SEQ ID No. 8, SEQ No. 9, respectively, wherein the forward primer, reverse primer of the MSP are the nucleotide sequences of SEQ ID No. 10 and SEQ ID No. 11, respectively, wherein the HBV DNA is quantified by real-time quantitative PCR using a forward primer, a reverse primer and a probe, wherein the forward primer and the reverse primer of the real-time quantitative PCR are nucleotide sequences selected from the group consisting of: (i) SEQ ID No. 28 and SEQ ID No. 29, respectively; (ii) SEQ ID No. 30 and SEQ ID No. 31, respectively; (iii) SEQ ID No. 32 and SEQ ID No. 33, respectively; (iv) SEQ ID No. 34 and SEQ ID No. 35, respectively; (v) SEQ ID No. 36 and SEQ ID No. 37, respectively.

In another embodiment, the one or more regions of HBV DNA is CpG island 3, wherein the forward primer, reverse primer and the probe of the BSP are nucleotide sequences of SEQ ID No. 12, SEQ ID No. 13, SEQ No. 14, respectively, wherein the forward primer, reverse primer and the probe of the MSP are the nucleotide sequences of SEQ ID No. 15, SEQ ID No. 16 and SEQ ID No. 17, respectively, wherein the HBV DNA is quantified by real-time quantitative PCR using a forward primer, a reverse primer and a probe, wherein the forward primer, the reverse primer and the probe of the real-time quantitative PCR are nucleotide sequences of SEQ ID No. 38, SEQ ID No. 39 and SEQ ID No. 40, respectively.

In another embodiment, the MSP is a two-step MSP and the one or more regions of HBV DNA is CpG island 3, wherein the forward primer, reverse primer and the probe of the BSP are nucleotide sequences of SEQ ID No. 12, SEQ ID No. 13, SEQ No. 14, respectively, wherein the forward primer, reverse primer of the first step MSP are nucleotide sequences of SEQ ID No. 18 and SEQ ID No. 16, respectively, wherein the forward primer, reverse primer of the second step MSP are nucleotide sequences of SEQ ID No. 19 and SEQ ID No. 20, respectively, wherein the HBV DNA is quantified by real-time quantitative PCR using a forward primer, a reverse primer and a probe, wherein the forward primer, the reverse primer and the probe of the real-time quantitative PCR are nucleotide sequences of SEQ ID No. 38, SEQ ID No. 39 and SEQ ID No. 40, respectively.

In another embodiment, the MSP is a two-step MSP and the one or more regions of HBV DNA is CpG island 3, wherein the forward primer, reverse primer and the probe of the BSP are nucleotide sequences of SEQ ID No. 12, SEQ ID No. 13, SEQ No. 14, respectively, wherein the forward primer, reverse primer of the first step MSP are nucleotide sequences of SEQ ID No. 21 and SEQ ID No. 22, respectively, wherein the forward primer, reverse primer and the probe of the second step MSP are nucleotide sequences of SEQ ID No. 21, SEQ ID No. 23 and SEQ ID No. 24, respectively, wherein the HBV DNA is quantified by real-time quantitative PCR using a forward primer, a reverse primer and a probe, wherein the forward primer, the reverse primer and the probe of the real-time quantitative PCR are nucleotide sequences of SEQ ID No. 38, SEQ ID No. 39 and SEQ ID No. 40, respectively.

Another aspect of the present application is a kit for detecting the presence or absence of hepatitis B virus (HBV)-associated hepatocellular carcinoma (HCC) in a mammal, comprising:
(i) A forward primer and a reverse primer for a quantitative bisulfite specific PCR (BSP) to quantify bisulfite-treated HBV DNA;
(ii) A forward primer and a reverse primer for a quantitative methylation specific PCR (MSP); and
(iii) A forward primer and a reverse primer to quantify HBV DNA by real-time quantitative PCR.

In one embodiment, the kit further comprises a probe for BSP, a probe for MSP and a probe for he real-time quantitative PCR, wherein the forward primer, the reverse primer and the probe for BSP are nucleotide sequences of SEQ ID No. 1, SEQ ID No. 2, SEQ No. 3, respectively, wherein the forward primer, reverse primer and the probe of the MSP are nucleotide sequences of SEQ ID No. 4, SEQ ID No. 5, SEQ No. 6, respectively, wherein the forward primer, reverse primer and the probe for the real-time quantitative PCR are nucleotide sequences of SEQ ID No. 25, SEQ ID No. 26 and SEQ No. 27, respectively.

In another embodiment, the kit further comprises a probe for BSP, wherein the forward primer, the reverse primer and the probe for BSP are nucleotide sequences of SEQ ID No. 7, SEQ ID No. 8, SEQ No. 9, respectively, wherein the forward primer and the reverse primer for MSP are nucleotide sequences of SEQ ID No. 10 and SEQ ID No. 11, respectively, wherein the forward primer and the reverse primer for the real-time quantitative PCR are nucleotide sequences selected from the group consisting of: (i) SEQ ID No. 28 and SEQ ID No. 29, respectively; (ii) SEQ ID No. 30 and SEQ ID No. 31, respectively; (iii) SEQ ID No. 32 and SEQ ID No. 33, respectively; (iv) SEQ ID No. 34 and SEQ ID No. 35, respectively; (v) SEQ ID No. 36 and SEQ ID No. 37, respectively.

In another embodiment, the kit further comprises a probe for BSP, a probe for MSP and a probe for he real-time quantitative PCR, wherein the forward primer, the reverse primer and the probe for BSP are nucleotide sequences of SEQ ID No. 12, SEQ ID No. 13, SEQ No. 14, respectively, wherein the forward primer, the reverse primer and the probe for MSP are nucleotide sequences of SEQ ID No. 15, SEQ ID No. 16, SEQ No. 17, respectively, wherein the forward primer, the reverse primer and the probe for the real-time quantitative PCR are nucleotide sequences of SEQ ID No. 38, SEQ ID No. 39 and SEQ No. 40, respectively.

In another embodiment, the kit further comprises a probe for BSP and a probe for he real-time quantitative PCR, wherein the MSP is a two-step MSP, wherein the forward primer, reverse primer and the probe of the BSP are nucleotide sequences of SEQ ID No. 12, SEQ ID No. 13, SEQ No. 14, respectively, wherein the forward primer, reverse primer of the first step MSP are nucleotide sequences of SEQ ID No. 18 and SEQ ID No. 16, respectively, wherein the forward primer, reverse primer of the second step MSP are nucleotide sequences of SEQ ID No. 19 and SEQ ID No. 20, respectively, wherein the forward primer, the reverse primer and the probe for the real-time quantitative PCR are nucleotide sequences of SEQ ID No. 38, SEQ ID No. 39 and SEQ No. 40, respectively.

In another embodiment, the kit further comprises a probe for BSP and a probe for he real-time quantitative PCR, wherein the MSP is a two-step MSP, wherein the forward primer, reverse primer and the probe of the BSP are nucleotide sequences of SEQ ID No. 12, SEQ ID No. 13, SEQ No. 14, respectively, wherein the forward primer, reverse primer of the first step MSP are nucleotide sequences of SEQ ID No. 21 and SEQ ID No. 22, respectively, wherein second step MSP further comprising a probe, wherein the forward primer, reverse primer and the probe of the second step MSP are nucleotide sequences of SEQ ID No. 21, SEQ ID No. 23 and SEQ ID No. 24, respectively, wherein the forward primer, the reverse primer and the probe for the real-time quantitative PCR are nucleotide sequences of SEQ ID No. 38, SEQ ID No. 39 and SEQ No. 40, respectively.

Another aspect of the present application is a method of quantifying HBV DNA, comprising: amplifying and quantifying HBV DNA by real-time quantitative PCR assays using a forward primer and a reverse primer, wherein the forward primer and the reverse primer of the real-time quantitative PCR are nucleotide sequences selected from the group consisting of: (i) SEQ ID No. 25 and SEQ ID No. 26, respectively; (ii) SEQ ID No. 38, SEQ ID No. 39, respectively; (iii) SEQ ID No. 28 and SEQ ID No. 29, respectively; (iv) SEQ ID No. 30 and SEQ ID No. 31, respectively; (v) SEQ ID No. 32 and SEQ ID No. 33, respectively; (vi) SEQ ID No. 34 and SEQ ID No. 35, respectively; (vii) SEQ ID No. 36 and SEQ ID No. 37, respectively.

In another embodiment, the forward primer and the reverse primer are the nucleotide sequences of SEQ ID No. 25 and SEQ ID No. 26, respectively, wherein the real-time quantitative PCR assay further utilizes a probe, wherein the probe is nucleotide sequence of SEQ ID No. 27.

In another embodiment, the forward primer and the reverse primer are the nucleotide sequences of SEQ ID No. 38 and SEQ ID No. 39, respectively, wherein the real-time quantitative PCR assay further utilizes a probe, wherein the probe is nucleotide sequence of SEQ ID No. 40.

BRIEF DESCRIPTION OF THE DRAWINGS

FIG. 1 is a diagram of the HBV genome (NC_003977.1) indicating the location of the three CpG islands and the primers for PCR assays used in the present application.

FIG. 6 shows the detection of methylated CpG 3 DNA by the a short amplicon MSP assay, in urine of patients with HBV infection as a biomarker to distinguish HCC from cirrhosis.

DETAILED DESCRIPTION OF ILLUSTRATIVE EMBODIMENTS

The present subject matter may be understood more readily by reference to the following detailed description taken in connection with the accompanying examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it is understood that the particular value forms another embodiment. All ranges are inclusive and combinable.

Hepatitis B virus (HBV) is a hepatotropic virus causing hepatitis, cirrhosis and hepatocellular carcinoma (HCC). In patients, HBV DNA circulates in blood as virion DNA and exists in hepatocytes both as nuclear form (episomal cccDNA and integrated DNA) and as cytoplasmic core DNA form. It has been reported that HBV infection up-regulates DNA (cytosine-5) methyltransferases and thus induces epigenetic changes in the host cells. Understanding the methylation status of the HBV DNA in its different forms can potentially provide insight into the pathogenesis of HBV-related liver diseases including hepatocarcinogenesis. Previous studies conducted in patient serum and in cell cultures have demonstrated that the CpG islands of HBV virion DNA are in the unmethylated state, and cccDNA methylation has been extensively studied for its role in the regulation of transcription, but very few studies have investigated the methylation status of the HBV DNA in various disease stages of human liver tissues.

Figure 3:
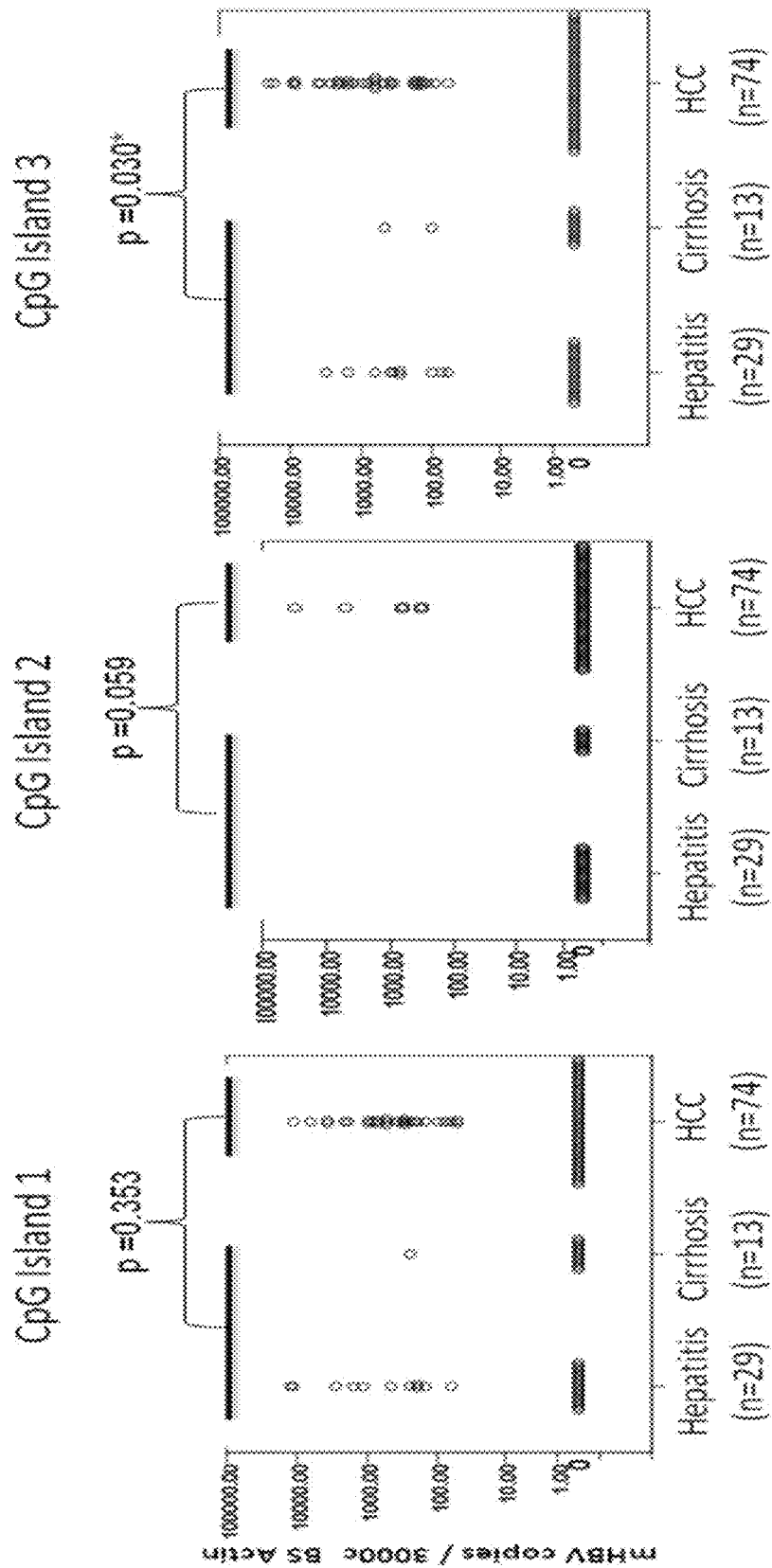
FIG. 3 shows the quantitative analysis of HBV DNA methylation in infected diseased livers.

The discovery of the association between CpG island 3 methylation and HCC development is illustrated in FIGS. 3 to 7. FIG. 3 shows the methylation profile of CpG island 3 in different liver diseases including hepatitis, cirrhosis, and HCC by bisulfite PCR sequencing, suggesting that the methylation of the CpG island 3 is associated with HCC development; Thus, it can be a potential biomarker for the early detection of HCC and can be used for HCC screening using urine as body fluid as described in FIGS. 5 to 7.

FIG. 1 is a diagram of the HBV genome (NC_003977.1) indicating the location of the three CpG islands and the primers for PCR assays used in the present application. Black rectangles represent the HBV regions; polymerase, enhancer II, basal core promoter, precore, preS and X gene. These regions correspond to the dashed line representing the HBV genome with vertical gray bars indicating nucleotide location. The three CpG islands are indicated by horizontal grey bars below the dashed line. The CpG site distribution in the HBV genome (solid black line) is depicted by vertical grey lines each representing an individual CpG site. The boxes with black borders on the CpG distribution map indicate the regions targeted by the bisulfite sequencing PCR and are enlarged below for better resolution of the CpG sites. The numbering of the CpG sites in the enlarged regions corresponds to that used in FIG. 2. The arrows below this enlarged bisulfite sequencing region indicate primer locations for the specified PCR assays. Detailed primer information is in Table 3. FIG. 1 shows CpG Islands reports potential CpG island regions using the method described by Gardiner-Garden and Frommer (1987). The calculation is performed using a 200 bp window moving across the sequence at 1 bp intervals. CpG islands are defined as sequence ranges where the Obs/Exp value is greater than 0.6 and the GC content is greater than 50%.

Figure 2:
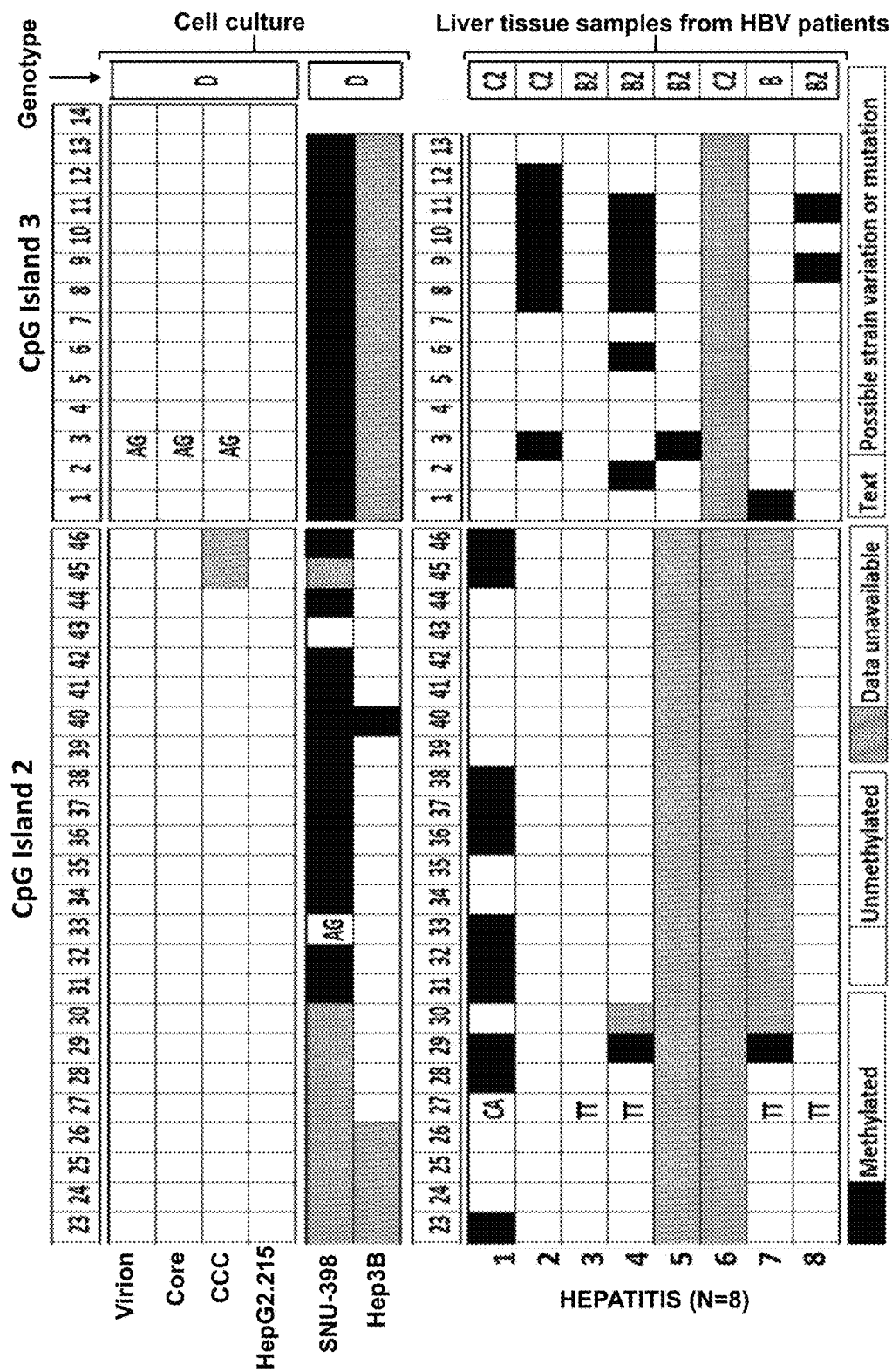
FIG. 2 is the methylation profile of the HBV genome by bisulfite sequencing of DNA isolated from cell cultures or liver tissues from HBV patients.
Figure 2:
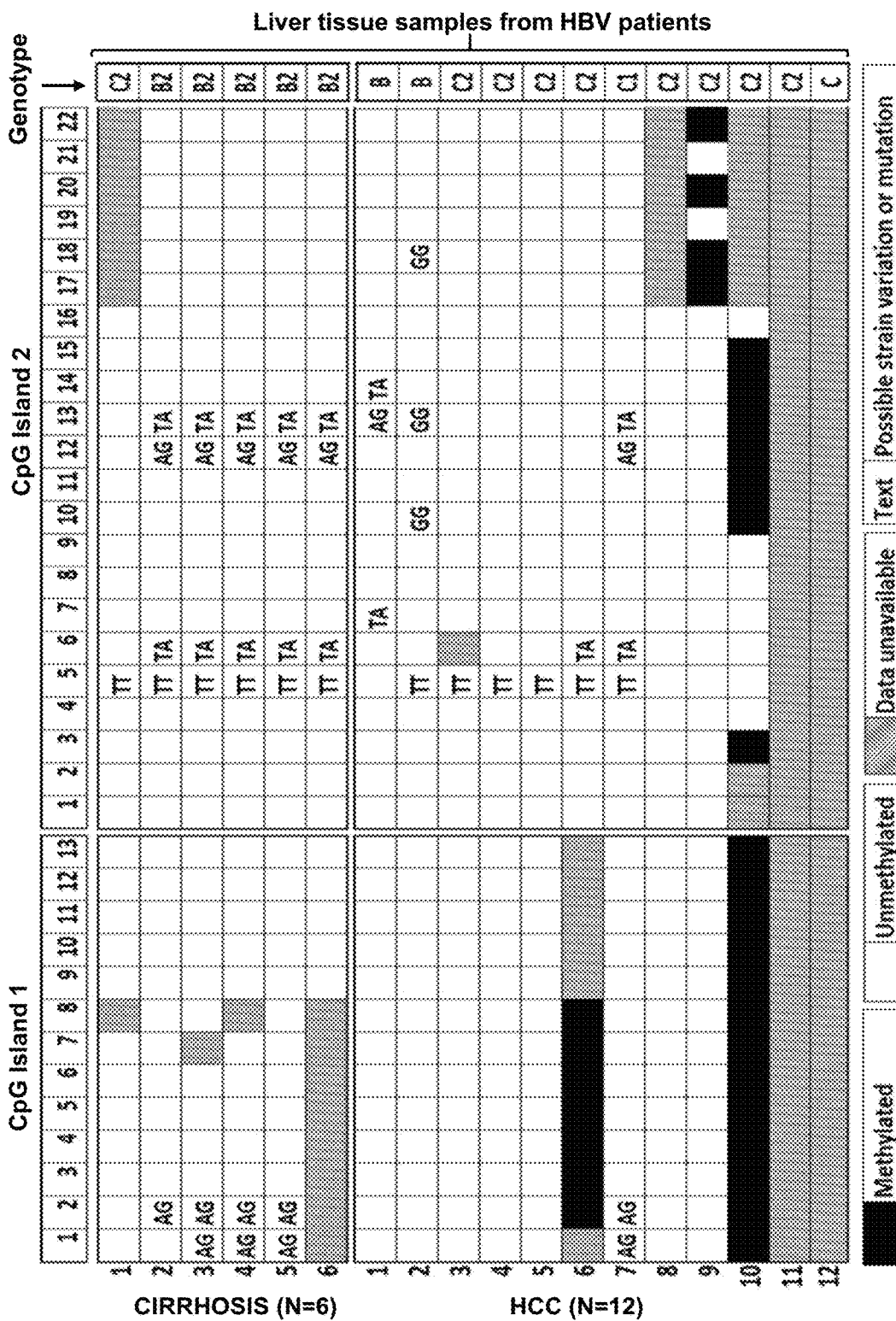
Figure 2:
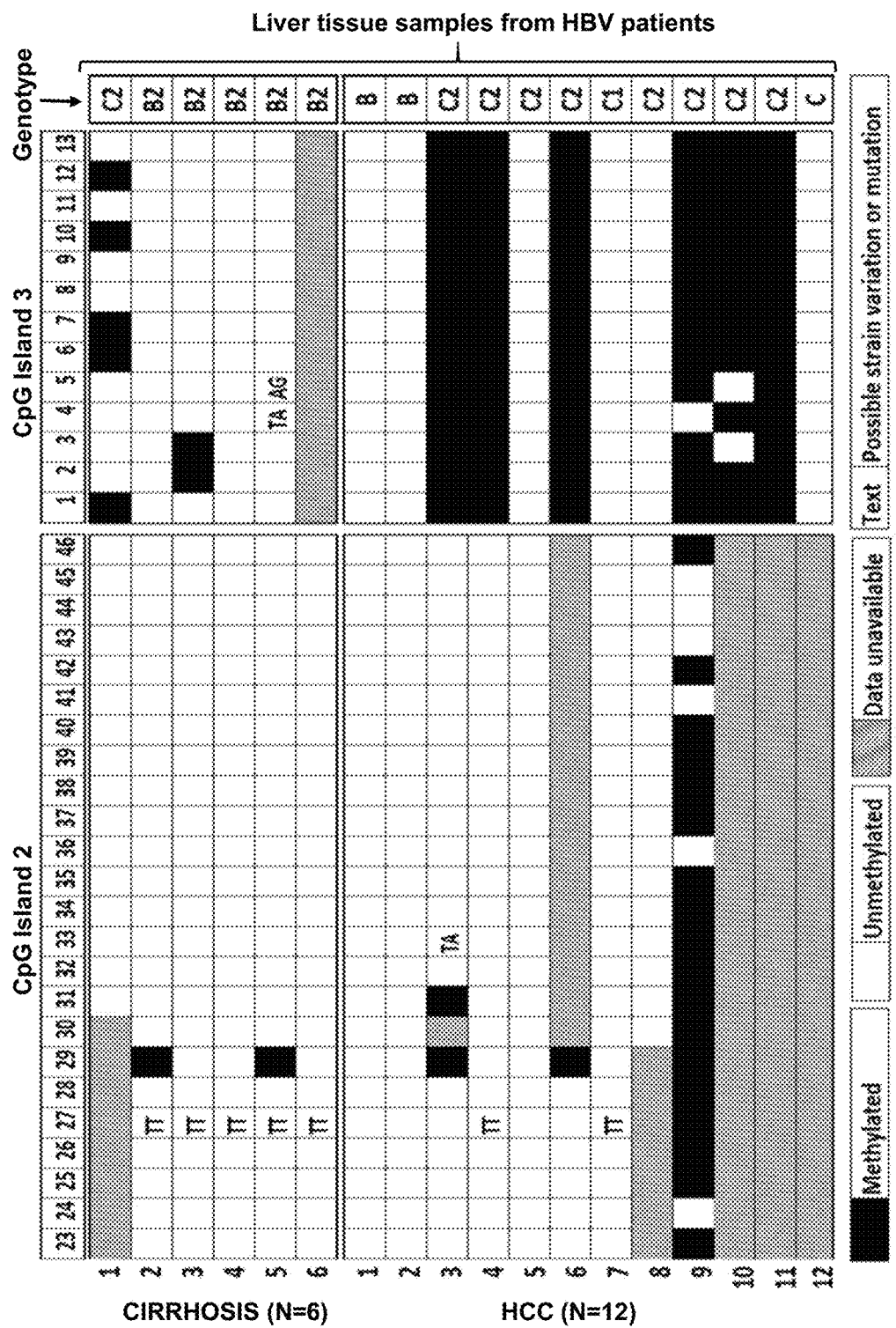
Figure 2:
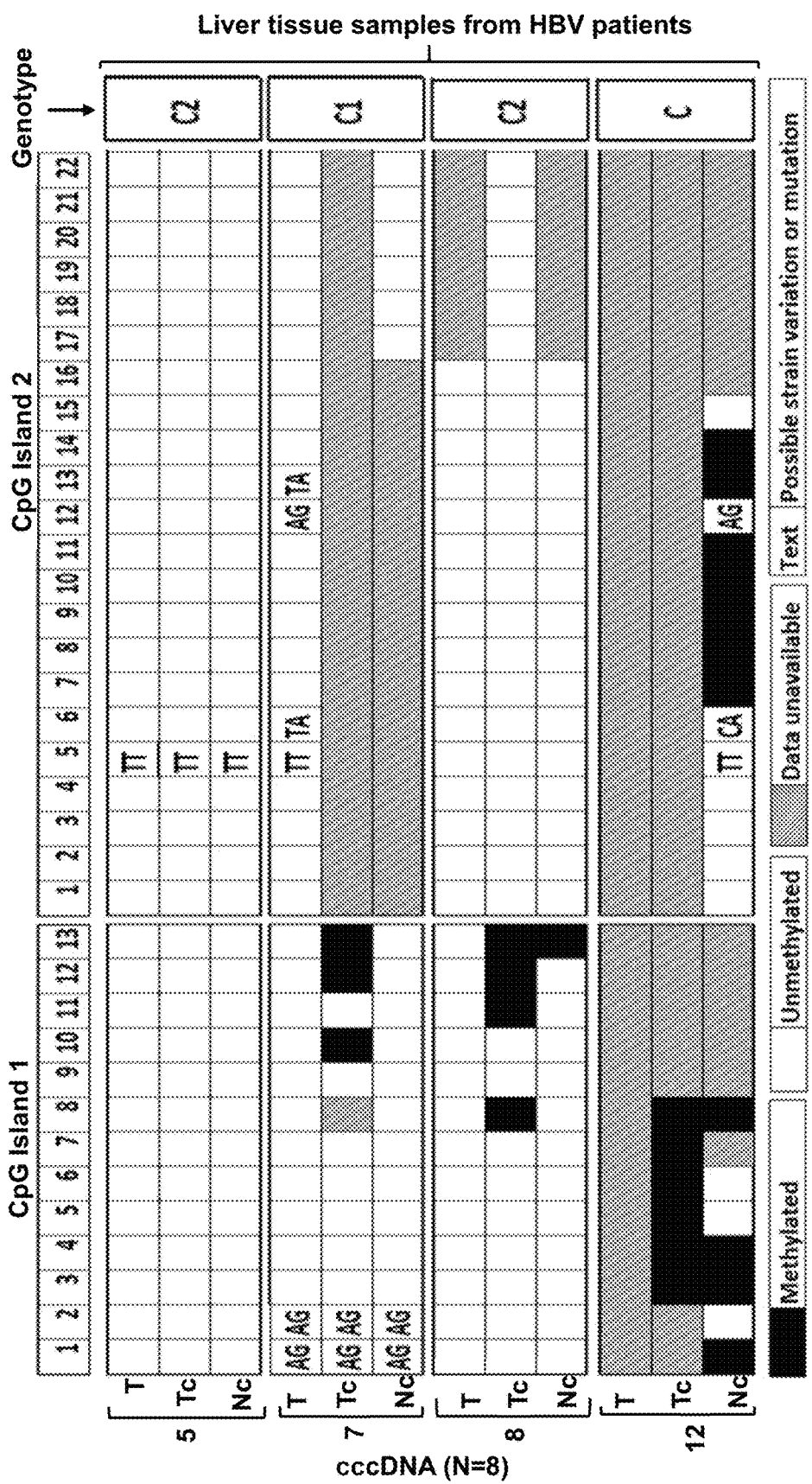
Figure 2:
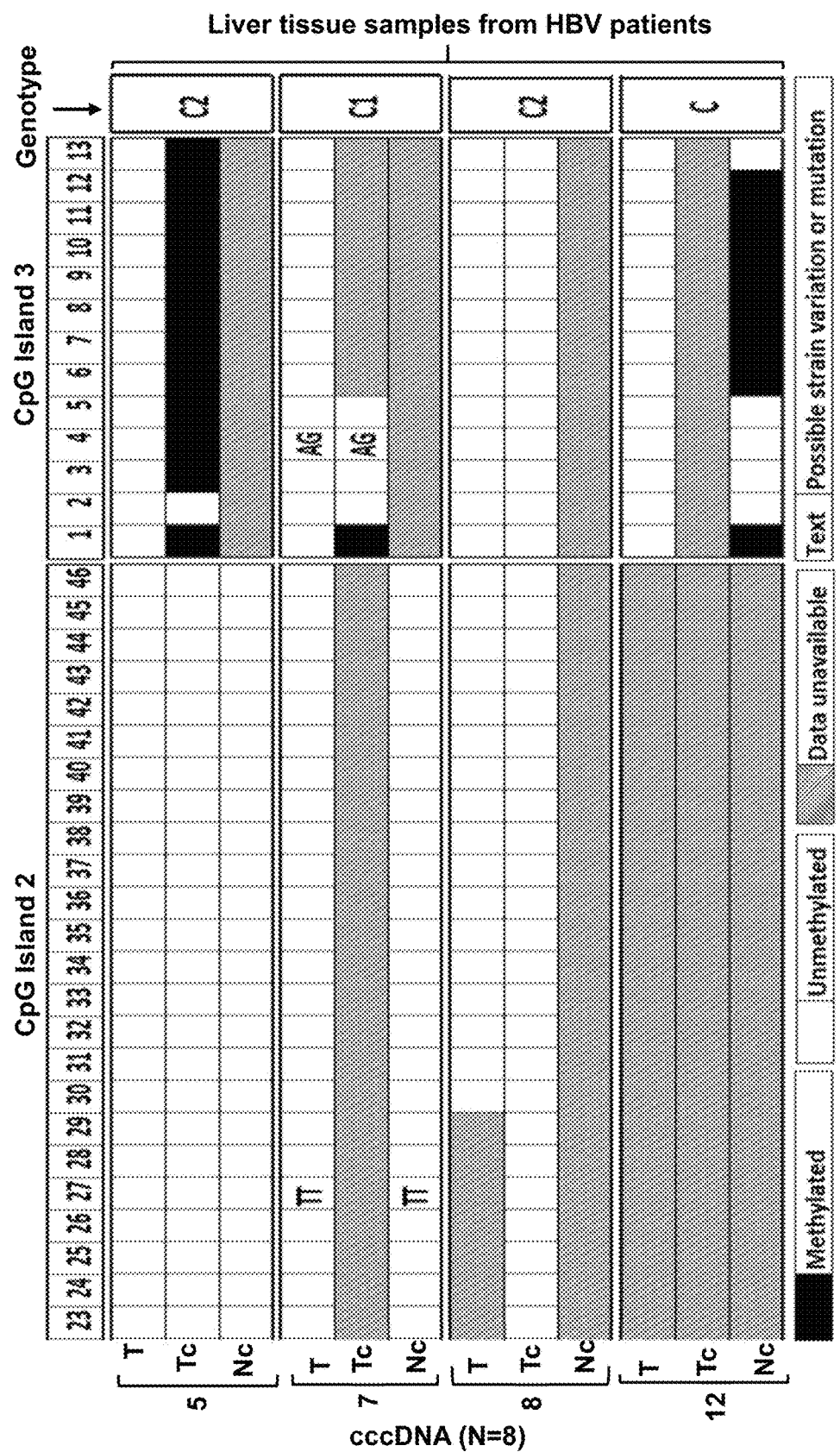

As shown in FIG. 2, we did not detect methylation in virions. No detectable methylation was identified either in cytoplasmic core, the cccDNA/extra-chromosomal nuclear DNA isolated from HepDE19 cells, or the total DNA from the HepG2.2.15 cell culture. For the integrated DNA, when the DNA was derived from SNU-398 cells, which contain the transcriptionally repressed HBV genome, DNA methylation was detected in all the HBV DNA amplified by BS-PCR primers. When the integrated HBV DNA from Hep3B was analyzed, which is known to express the S antigen, preS and X transcripts, the HBV DNA was mostly unmethylated except for the CpG island 1, which was mostly methylated.

As shown in FIG. 2, there are regions marked as "data unavailable" such as the CpG island 1 and the 5' end of the CpG island 2 of the HBV genome in SNU-398 cells, and the middle of the CpG island 2 and CG3 of the HBV genome in Hep3B cells. These were the regions that BS-PCR reactions either failed to generate specific PCR products for DNA sequencing, or the sequencing data were unreadable despite multiple attempts. Many attempts using multiple sets of primers for both untreated and BS-treated DNA were unable to amplify detectable PCR products, perhaps due to the possibility that DNA sequences in these areas might be either deleted during HBV integration, or altered to the extent that none of the tested primers had sufficient homology to prime the PCR reaction. As compared to the reference genome, few nucleotide variants were noted in Hep3B and SNU-398 cells.

To obtain the comprehensive methylation profiles for each CpG site of all three known CpG islands in the HBV genomes from both cell cultures and infected tissues, we chose to perform bisulfite PCR (BS-PCR) sequencing on a small set of tissue samples (8 hepatitis, 6 cirrhosis, and 12 HCC based on the quantity of DNA available to us. The clinicopathological information is summarized in Supplementary Table S1 in Jain et. al., 2015. In order to design the suitable BS-specific primers, we began by performing the genotyping of the HBV DNA in each tissue sample. We then designed BS primers covering three CpG islands in various genotypes of the HBV genome, to amplify the BS-treated HBV DNA from cell cultures and tissue samples (FIG. 1, Table 1).

FIG. 2 is the Methylation profile of the HBV genome by bisulfite sequencing of DNA isolated from cell cultures or liver tissues from HBV patients. Each box indicates one CpG site (filled, methylated; open, unmethylated; hatch, data unavailable; text, possible sequence variations at CpG site). Top panel shows the results from cell cultures—HepDES19 derived virion, core, cccDNA and total HepG2.215 DNA, followed by DNA isolated from two HBV-integrated HCC cell lines SNU-398 and Hep3B. Subsequent three panels show the results from clinical samples—hepatitis, cirrhosis and HCC aligned to HBV genotype C virus (NC_003977.1). Bottom panel shows results from total tumor tissue DNA (T), cccDNA from tumor ($T_C$) and adjacent non-HCC tissue ($N_C$). The genotype of each sample is indicated on the right.

We next performed BS-PCR sequencing analysis on the disease tissues. As aforementioned, we developed a total of 24 sets of primers based on genotyping data, 10 sets for the CpG island 1, 12 sets for the CpG island 2, and 2 sets for the CpG island 3. Although we were able to generate specific PCR products from most of the HBV infected tissue DNA to obtain BS sequencing data for most of the CpG sites, there were still regions in the genomes that failed to be amplified, regardless of multiple attempts. Thus, the methylation status was unavailable for those regions, as indicated in the FIG. 2. Nevertheless, the information obtained is sufficient for statistical analysis of the methylation of each CpG island comparing HCC tissues to hepatitis and cirrhosis.

To compare DNA methylation in different disease groups, we calculated the percentage of CpG sites that were found to contain detectable levels of methylation, which were analyzed for each disease group within each CpG island (Table 1). A low level of methylation was detected in all three CpG islands in the hepatitis samples (6.6%, 6%, and 17.5% in CpG island 1, CpG island 2 and CpG island 3, respectively), whereas, the HBV DNA detected in cirrhosis tissue was mostly unmethylated in CpG island 1 (0%) and CpG island 2 (0.8%), and a low level of methylation was found in CpG island 3 (10.8%). Interestingly, in the HCC samples, although a low percentage of methylation was detected in CpG island 1 and CpG island 2 (16.1% and 8%, respectively), 52.5% of the CpG sites in CpG island 3 were found to be methylated. Furthermore, every CpG site of CpG island 3, except for three, were found to be methylated in 6 of the 12 HCC samples that had methylation. Comparing these three CpG islands within HCC samples, the CpG island 3 is the most methylated (p<0.001, comparing CpG island 3 to CpG island 1 and CpG island 3 to CpG island 2, by Fisher's two-tailed exact test). When comparing the extent of methylation of CpG island 3 among three disease groups, HCC was significantly higher than that of hepatitis and cirrhosis (p<0.0001, Fisher's two-tailed exact test, Table 1). Similarly, HCC also had significantly higher levels of methylation in CpG island 1 and CpG island 2, as compared to hepatitis and cirrhosis (CpG island 1, p=0.0007; CpG island 2, p=0.0046, Fisher's two-tailed exact test, Table 1). There were few nucleotide variants with respect to the reference genome (Genbank # NC 003977.1), as noted in FIG. 2, which were mostly in CpG island 2 and the first 2 CpG sites of CpG island 1.

U-test). We also observed no significant differences in the levels of CpG island 3 methylation in the HBV-HCC samples that were categorized by their HCV status (p=0.695, Kruskal Wallis test). Interestingly, we observed higher levels of methylation in CpG island 1 and CpG island 3 of hepatitis samples as compared to cirrhosis samples, although only methylation of CpG island 1 was significantly higher in hepatitis samples as compared to cirrhosis samples (p=0.05, Mann Whitney U test). No methylation was observed in either hepatitis or cirrhosis samples in CpG island 2.

TABLE 1

HBV DNA methylation in various HBV-infected livers by BS-PCR sequencing.

| | CpG island | | |
|---|---|---|---|
| Percent of methylated CpG sites[e] | 1 | 2 | 3 |
| Hepatitis | 6.6% (5/76) | 6.0% (15/250) | 17.5% (16/91) |
| Cirrhosis | 0% (0/60) | 0.8% (2/236) | 10.8% (7/65) |
| HCC | 16.1% (20/124) | 8.0% (32/398) | 52.5% (75/143) |
| p value[#] | 0.0007 | 0.0046 | <0.0001 |
| HCC vs. (Hepatitis and Cirrhosis) | | | |

[e]The percent of methylated CpG sites was calculated as the number of methylated CpG sites detected/total CpG sites with valid BS sequencing data (methylated + unmethylated) shown in FIG. 2.
[#]Fisher's two-tailed exact test.

FIG. 3 is the quantitative analysis of HBV DNA methylation in infected diseased livers. Scatter plots of the quantity of methylated HBV DNA detected by qMSP assays for each CpG island. Each data point represents one sample and is the average of two duplicate assays per input of 3000 copies of BS-actin DNA. p values indicate the statistical comparison between HCC and non-HCC (hepatitis and cirrhosis) samples for each CpG island by Mann-Whitney U test.

Figure 4:
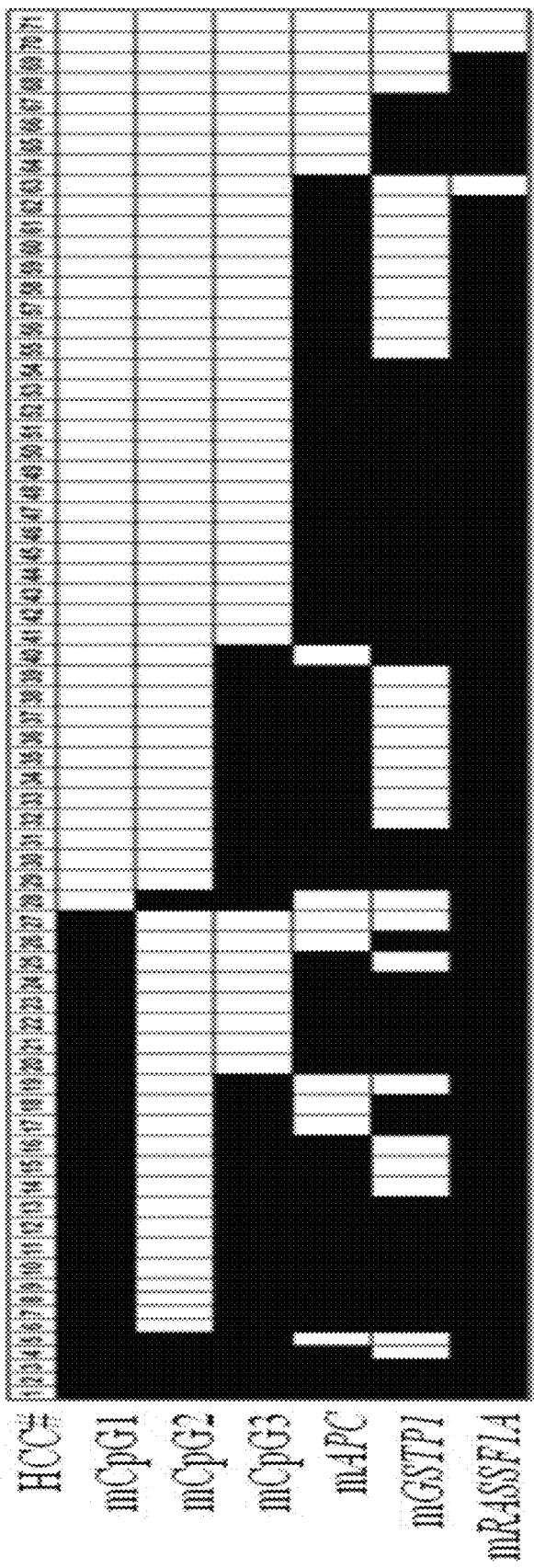
FIG. 4 shows comparison of HBV and host gene methylation in HBV-HCC.

To evaluate whether the extent of DNA methylation was associated with the progression of liver diseases, we developed quantitative MSP (qMSP) assays for each CpG island to measure the DNA methylation in a larger sample size. As some of the HBV infected tissues may not contain any detectable HBV DNA, each DNA sample was first subjected to the quantitative HBV DNA PCR assays for CpG island 1 and CpG island 3, as described in the Materials and Methods. Only samples positive for at least one HBV DNA assay were subjected to methylation analysis. The clinicopathological characteristics of the study subjects (74 HCC, 29 hepatitis and 13 cirrhosis) are listed in Supplementary Table S2 of Jain et. al., 2015. Three qMSP assays were performed to quantify the level of methylation for each of the three CpG islands. As shown in FIG. 3, there is no statistically significant difference (p>0.05, Mann Whitney U-test) between the methylation levels of HCC and non-HCC (hepatitis and cirrhosis) tissues in CpG island 1 and CpG island 2. In contrast, methylation of CG3 in HCC tissues (mean=1250.5, standard deviation=3504) was significantly higher than in non-HCC tissue (hepatitis and cirrhosis, mean=174.6, standard deviation=534) tissues (p<0.05, Mann Whitney U-test). Of the 74 HBV-HCC cases, 9 are HCV positive, 45 are HCV negative, and the HCV status of the remaining 20 is unknown. HCV infection is also known to cause aberrant methylation and can be a potential confounding factor. Hence, we compared the methylation levels of CpG island 3 in HBV-positive, HCV-negative HCC (n=45) to HBV-infected hepatitis and cirrhosis samples. The results confirmed that methylation of CpG island 3 in this subset of HCC tissues was still significantly higher than in hepatitis and cirrhosis tissues (p<=0.05, Mann Whitney FIG. 4 shows comparison of HBV and host gene methylation in HBV-HCC. More specifically, it shows distribution of HBV and host genome methylation categorized by their serum alfa-fetoprotein (AFP) levels in HBV-HCC samples (n=68). Each column represents one sample. In the AFP row, filled rectangles indicate serum AFP greater than 20 ng/ml while open rectangles indicate a serum AFP level less than 20 ng/ml. Filled rectangles in mCpG1, mCpG2, mCpG3, mAPC, mGSTP1 and mRASSF1A indicate methylated status while open rectangles indicate no detectable methylation.

It has been shown that HBV infection upregulates DNA methyltransferase activity, which leads to simultaneous methylation of HBV DNA and host CpG islands in cell culture experiments. DNA methylation of many tumor suppressor genes has been associated with carcinogenesis. Among these known tumor-associated, aberrant-methylation events, methylation of the APC, GSTP-1, and RASSF1A genes were found to be associated with HCC. It is therefore of interest to investigate whether the HBV DNA methylation correlates with these three HCC-associated host gene methylation events. BS-treated HCC DNA was subjected to previously developed quantitative MSP assays for these three genes (FIG. 4). The Spearman's rho test was used to determine the correlation co-efficiency (Table 2). When comparing methylation of genes within the host genome, there is a significant correlation (p<0.01) between either of the two host genes, and within the HBV genome in HBV-related HCC, there is also a significant correlation (p<0.01) between CpG island 1 and CpG island 3 of the HBV genome in HCC. The only significant correlation between HBV DNA and host genes was found between methylation of CpG island 3 and RASSF1A.

TABLE 2

Correlation of DNA methylation of the HBV genome with three known HCC associated host genes in HCC tissue.

| Genes | Statistic | mCpG1 (n = 74) | mCpG3 (n = 74) | mAPC (n = 71) | mGSTP1 (n = 71) |
|---|---|---|---|---|---|
| mCpG3 (n = 74) | Spearman's rho | .471 | | | |
|  | p value | <0.001 | | | |
| mAPC (n = 71) | Spearman's rho | 0.098 | 0.094 | | |
|  | p value | 0.418 | 0.435 | | |
| mGSTP1 (n = 71) | Spearman's rho | 0.233 | −0.008 | .324 | |
|  | p value | 0.051 | 0.947 | 0.006 | |
| mRASSF1A (n = 71) | Spearman's rho | 0.132 | .269 | .510 | .513 |
|  | p value | 0.271 | 0.023 | <0.001 | <0.001 |

Cell-free circulating DNA has been shown to reflect characteristics of tumor DNA (Chan et al., 2008; Diehl et al., 2008; Forshew et al., 2012; Pathak, Bhutani, Kumar, Mohan, & Guleria, 2006; Stroun, Anker, Lyautey, Lederrey, & Maurice, 1987; Stroun et al., 1989; Tsutsui et al., 2010; Utting, Werner, Dahse, Schubert, & Junker, 2002; Wong, Zhang, Lai, Lau, & Lo, 2003; Wu et al., 2002; Yen et al., 2009; Ziegler, Zangemeister-Wittke, & Stahel, 2002) and are mostly fragmented in 1-2 nucleosomal sizes in some body fluids such as plasma and urine. Attempts have been made to detect cancer genetically in blood, but developing a test of sufficient sensitivity has been challenging (Chan et al., 2008; Kirk et al., 2005; Lleonart et al., 2005; Tsutsui et al., 2010; Wong et al., 2003). Thus, technologies must be developed that would be capable of isolating circulating DNA in quantities sufficient for the analysis of biomarkers and of detecting circulating DNA markers with a sensitivity and specificity sufficient to translate the discovered biomarkers for application in HCC screening.

Figure 5:
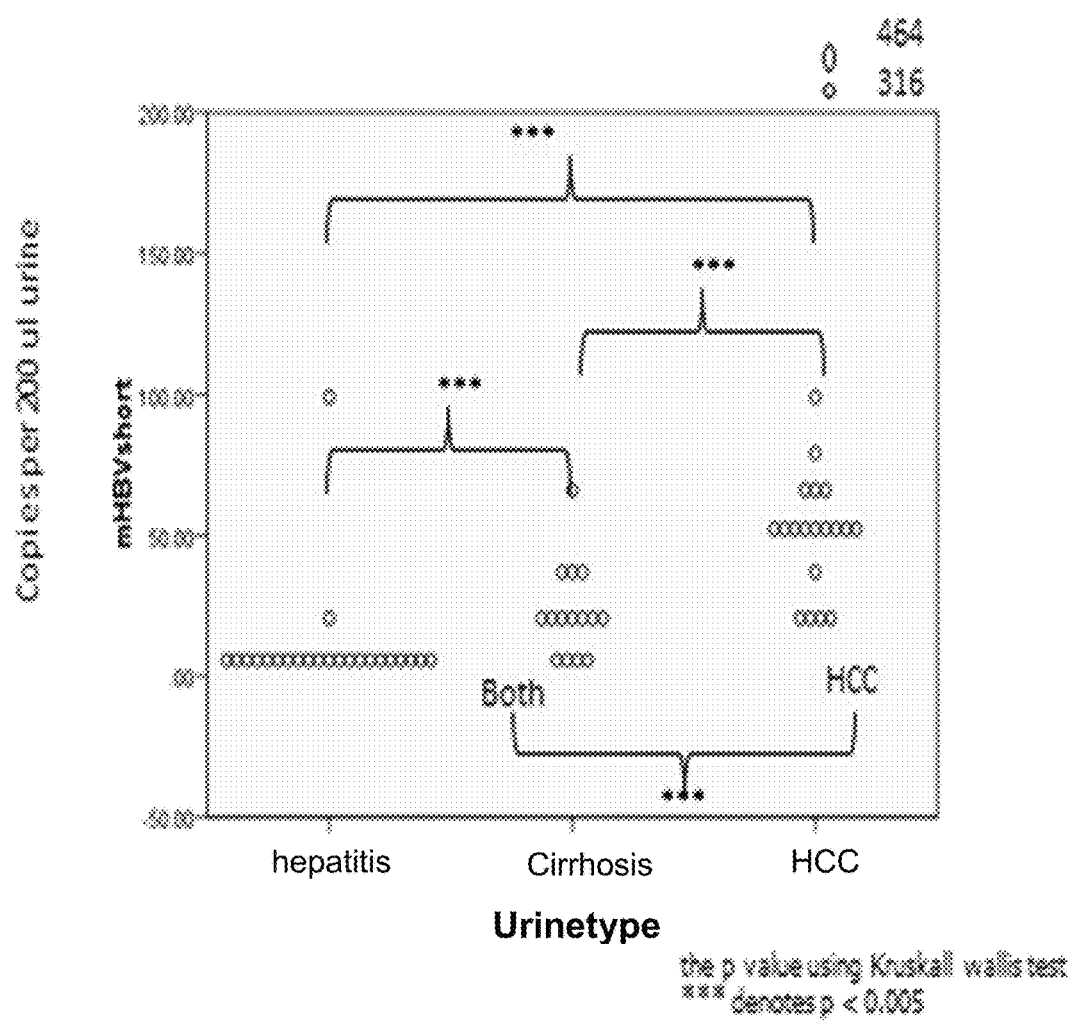
FIG. 5 shows the comparison of the amount of methylated HBV CpG island 3 DNA determined by a short amplicon MSP assay, in urine of patients with HBV-related liver diseases.

Urine has been used as a source of reporter molecules for urinary tract diseases with great clinical benefit. Urine-based tests are non-invasive and very patient-friendly. The use of urine as a biological fluid for cancer detection is now possible with advances in molecular biomarker assays and recent findings that tumor-derived DNA in circulation can be detected in urine as low-molecular-weight (LMW) urine DNA, which is less than 300 bp in size (Su et al., 2004). A short amplicon MSP assay was developed (as described in the paragraph 61) to quantify the methylated HBV CpG island 3 DNA in urine and other body fluids. FIG. 5 shows the amount of methylated HBV CpG island 3 DNA determined by a short amplicon MSP assay (as described in the paragraph 61) in urine of patients with HBV-related liver diseases, compared with the amount of methylated HBV CpG island 3 in normal non-cancer subjects.

FIG. 6 shows the detection of methylated CpG 3 DNA by a short amplicon MSP assay (as described in the paragraph 61), in urine of patients with HBV infection as a biomarker to distinguish HCC from cirrhosis. The ROC curve was constructed and area under the curve (AUROC) was 0.867. In this small cohort, the AUROC of serum AFP was 0.798.

Figure 7:
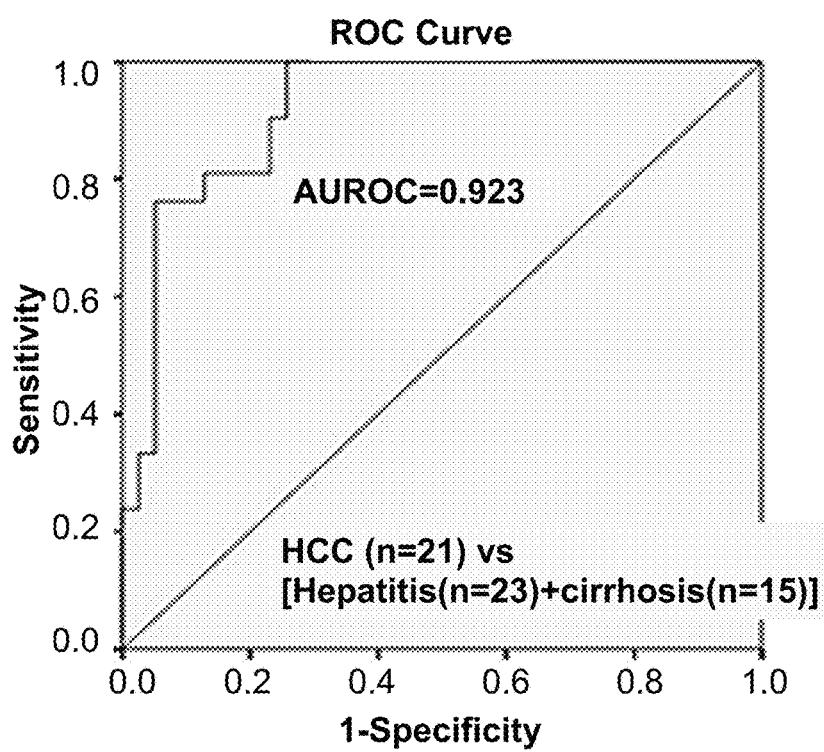
FIG. 7 shows the detection of methylated CpG 3 DNA by a short amplicon MSP assay, in urine of patients with HBV infection as a biomarker to distinguish HCC from hepatitis+ cirrhosis.

FIG. 7 shows the performance of methylated CpG 3 DNA as a DNA biomarker to distinguish HCC from non-HCC (hepatitis+cirrhosis) in urine of patients with HBV infection, assayed by a short amplicon MSP assay (as described in the paragraph 61). The ROC curve was constructed and AUROC was 0.923 to distinguish HCC from non-HCC in urine.

The term "nucleotide amplification reaction" refers to any suitable procedure that amplifies a specific region of polynucleotides (target) using primers. See generally Kwoh et al., Am. Biotechnol. Lab. 8:14 (1990; Kwoh et al., Proc. Natl. Acad. Sci. USA 86, 1173-1177 (1989); Lizardi et al., BioTechnology 6:1197-1202 (1988); Malek et al., Methods Mol. Biol., 28:253-260 (1994); and Sambrook et al., "Molecular Cloning: A laboratory Manual" (1989)).

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "effective amount," in the context of treatment of a disease or disorder refers to the amount of such molecule that is sufficient to inhibit the occurrence or ameliorate one or more clinical or diagnostic symptoms of the disease or disorder in a subject. The term "effective regime" refers to a combination of amount of the agent being administered and dosage frequency adequate to accomplish treatment or prevention of the disease or disorder.

Due to the imprecision of standard analytical methods, molecular weights and lengths of polymers are understood to be approximate values. When such a value is expressed as "about" X or "approximately" X, the stated value of X will be understood to be accurate to ±10%. are provided to assist in a further understanding of the inventions. Particular materials used, protocols and conditions are intended to be further illustrative of the inventions and should not be construed to limit the reasonable scope thereof.

Provided herein is a suitable method for detecting the presence or absence of a cancer in an individual by determining the level of DNA mutations and aberrant DNA methylation from the individual, comparing the level of DNA mutations and aberrant DNA methylation with a baseline level of DNA mutations and methylation found in one or more control samples from individuals known not to have the cancer, and correlating a finding of elevated methylation and DNA mutations in the individual with an enhanced likelihood that the individual has cancer. The cancer can be hepatocellular carcinoma (HCC) and the control can be non-HCC sample. The examples of genetic DNA mutations (listed in Table 3) and aberrant DNA methylation markers (listed in Table 3) that can be used for HCC screening using urine as body fluid.

Provided herein is a suitable method for detecting the presence or absence of HBV DNA in liver tissues or body fluids and whether the HBV DNA is methylated. The examples of oliogs used in each assay for detecting HBV DNA or bisulfite converted HBV DNA with the location of the oligos and conditions of the respective PCR reactions (listed in Table 3).

TABLE 3

Primer/Probe sequences and reaction parameters for quantitative PCR assays

| Location | HBV nt. (NC_003977.1) | Assay | Forward | Reverse | Probe/Detection format | PCR conditions |
|---|---|---|---|---|---|---|
| CpG Island 1 | 207-285 | BSP | HBV_BSC1F1: GGTTTTTTTTGTTGAT AAGAATTT (SEQ ID NO: 1) | HBV_BSC1R3: CCCCTAAAAAA ATTAAAAAAA A (SEQ ID NO: 2) | BSC1TQ:[6FAM]TTATAA TATTATAGAGTTTAGA TTYGTGTGGA[BHQ1] (SEQ ID NO: 3) | 95° C. 5 min, (95° C. 10 s 50° C. 15 s, 72° C. 10 s) × 50 cycles |
|  | 293-402 | MSP | HBV_C1F2B: ACGTGTTTTGGTTAA AATTCGTAGTTTTA (SEQ ID NO: 4) | HBV_C1R5B: AATATAATAAA ACGCGCAAAC ACATC (SEQ ID NO: 5) | C1MSTQ:[6FAM] GTTTTTTAATTTGTTTT GGTTATCGTTGATG [BHQ1] (SEQ ID NO: 6) | 95° C. 5 min, (95° C. 10 s 55° C. 30 s, 72° C. 10 s) × 50 cycles |
| CpG Island 2 | 1660-1733 | BSP | HBV_BSC2F1: GGATTTTTGGATTTT AGTAATGTT (SEQ ID NO: 7) | HBV_BSC2R3: CCAATCTTTAA ACAAACAATCT TTAA (SEQ ID NO: 8) | BSC2TQ:[6FAM]ATGTTA AYGATYGATTTTGAGG TATATTTTAA[BHQ1] (SEQ ID NO: 9) | 95° C. 5 min, (95° C. 10 s 53° C. 15 s, 72° C. 10 s) × 50 cycles |
|  | 1502-1579 | MSP | HBV_C2MF3: TGTCGTTTCGGTCGAT TAC (SEQ ID NO: 10) | HBV_C2MR3: CACGATCCGAC AAATAAAA (SEQ ID NO: 11) | SYBR Green | 95° C. 5 min, (95° C. 10 s 52° C. 30 s, 72° C. 10 s) × 45 cycles, melt [95° C. 5 s, 65° C. 60 s, 97° C. continuous], 40° C. 30 s |
| CpG Island 3 | 2161-2239 | BSP | HBV_BSC3F9: TTATGTTAATGTTAAT ATGGGTTTAAA (SEQ ID NO: 12) | HBV_BSC3R9.10: TTCTCTTCCAA AAATAAAAACA A (SEQ ID NO: 13) | C3BSTQ: [6FAM]TTAgATAATTAT Tg+Tgg+T+T+TA+TA+ T[BBQ] (SEQ ID NO: 14) | 95° C. 10 min, (95° C. 10 s, 52° C. 30 s, 72° C. 10 s) × 50 cycles |
|  | 2270-2412 | MSP | HBV_MSP2F: GTGTGGATTCGTATTT TTTTC (SEQ ID NO: 15) | HBV_MSP2R: GACGATTAAAA CCTTCGTCT (SEQ ID NO: 16) | C3AMSTQ: AACCTACCTCGTCGTCT AACAACAT (SEQ ID NO: 17) | 95° C. 10 min, (95° C. 10 s, 53° C. 30 s, 72° C. 10 s) × 45 cycles |
|  | 2370-2412 | MSP-Step 1 | HBT_SMF1: GCTCTTCGTGGTGTG GTGAAGAAGAATTT TTCGTTTC (SEQ ID NO: 18) | HBV_MSP2R1: GACGATTAAAA CCTTCGTCT (SEQ ID NO: 16) | N/A | 95° C. 5 min, (95° C. 10 s, 50° C. 30 s, 72° C. 30 s) × 27 cycles, 72° C. 4 min, 4° C. Hold |
|  |  | MSP-Step 2 | HBV_S2F1: TGTGTGAAGAAGAA TT (SEQ ID NO: 19) | HBV_S2R1: GACGATTAAAA CCTTC (SEQ ID NO: 20) | SYBR Green | 95° C. 5 min, (95° C. 10 s, 50° C. 15 s, 72° C. 10 s) × 45 cycles, Melting curve, 40° C. 30 s |
|  | 2375-2430 | MSP-Step 1 | C3_M_F1: AGAATTTTTCGTTTC GTAGAC (SEQ ID NO: 21) | C3.M_R3: AAAATCTTCTA CGACGCGACG ATTAA (SEQ ID NO: 22) | N/A | 95° C. 5 min, (95° C. 30 s, 50° C. 30 s, 72° C. 30 s) × 25/40 cycles; 72° C. 4 min, 4° C. hold |

TABLE 3-continued

Primer/Probe sequences and reaction parameters for quantitative PCR assays

| Location | HBV nt. (NC_003977.1) | Assay | Forward | Reverse | Probe/Detection format | PCR conditions |
|---|---|---|---|---|---|---|
| | | MSP-Step 2 | C3_M_F1: AGAATTTTTCGTTTC GTAGAC (SEQ ID NO: 21) | C3_M_R2: CTACGACGCGA CGATTAAAAC (SEQ ID NO: 23) | SYBR and Simple Probe FLQ-CG3.MSP SP: TCGTTTCGTAGACGAA GGT--PH (SEQ ID NO: 24) | 95° C. 5 min, (95° C. 10 s, 53° C. 30 s, 72° C. 10 s) × 45 cycles |
| | 246-309 | HBV DNA | HBV240F3: GTCTAGACTCGTGGT GGA (SEQ ID NO: 25) | HBVC240R1: TTTTGGCCAGG ACAC (SEQ ID NO: 26) | HBV240 TaqMan: [6FAM]CAATTTTCTAGG GGGAGCACCCAC[BHQ1] (SEQ ID NO: 27) | 95° C. 5 min, (95° C. 10 s, 54° C. 15 s, 72° C. 10 s) × 45 cycles |
| CpG Island 1 | 1583-1622 | | HBV_F_1583_1602: ACTTCGTTCACCTCT GCAC (SEQ ID NO: 28) | HBV_R_1604_1622: CACGGTGGT CTCCATGCTAC (SEQ ID NO: 29) | SYBR Green | 95° C. 5 min, (95° C. 10 s 60° C. 10 s, 72° C. 10 s) × 45 cycles, melt [95° C. 5 s, 65° C. 60 s, 97° C. continuous], 40° C. 30 s |
| CpG Island 2 | 1613-1671 | | HBV_F_1613_1629: GACCACGTGAACGC CC (SEQ ID NO: 30) | HBVRev1671_1654_Chr21: AGTCCAAGAGT CCTGTTGTCA AGACCTT (SEQ ID NO: 31) | SYBR Green | 95° C. 5 min, (95° C. 10 s 60° C. 10 s, 72° C. 10 s) × 45 cycles, melt [95° C. 5 s, 65° C. 60 s, 97° C. continuous], 40° C. 30 s |
| | 1633-1680 | | HBV_F_1633_1653: AGGTCTTGCCCAAGG TCTTAC (SEQ ID NO: 32) | HBV_R_1660_1680: TTGCTGAGA GTCCAAGAGTC C (SEQ ID NO: 33) | SYBR Green | 95° C. 5 min, (95° C. 10 s, 72° C. 10 s) × 45 cycles, melt [95° C. 5 s, 65° C. 60 s, 97° C. continuous], 40° C. 30 s |
| | 1685-1719 | | HBV_F_1685_1719: AACGACCGACCTTGA GGCATACTTC (SEQ ID NO: 34) | HBV_R_1713_1740: CTCCTCCCAGT CTTTAAACAAA CAGTC (SED ID NO: 35) | SYBR Green | 95° C. 5 min, (95° C. 10 s 60° C. 10 s, 72° C. 10 s) × 45 cycles, melt [95° C. 5 s, 65° C. 60 s, 97° C. continuous], 40° C. 30 s |
| | 1741-1791 | | TRGGGGAGGAGATAA GGTTAAAGGTC (SEQ ID NO: 36) | ATGCCTACAGC CTCCTAGTACA A (SEQ ID NO: 37) | SYBR Green | 95° C. 5 min, (95° C. 10 s, 65° C. 10 s, 72° C. 8 s) × 40 cycles, melt [95° C. 5 s, 65° C. 60 s, 97° C. continuous], 40° C. 30 s |
| CpG Island 3 | 2294-2347 | | HBV gp4 Fwd3a1: TACAGACCACCAAAT GCC (SEQ ID NO: 38) | HBV gp4 Rev3a: AACAACAGTA GTTTCCGAAG TGTTG (SEQ ID NO: 39) | HBV gp4 Probe 53bp: [6FAM]C+CTAT+C+T+T AT+CAA+CA+CTT+C[BHQ1] (SEQ ID NO: 40) | 95° C. 5 min, (95° C. 10 s 58° C. 15 s, 72° C. 15 s) × 45 cycles |

"+" indicates LNA nucleotide
"R" indicates A + G nucleotides

Figure 8:
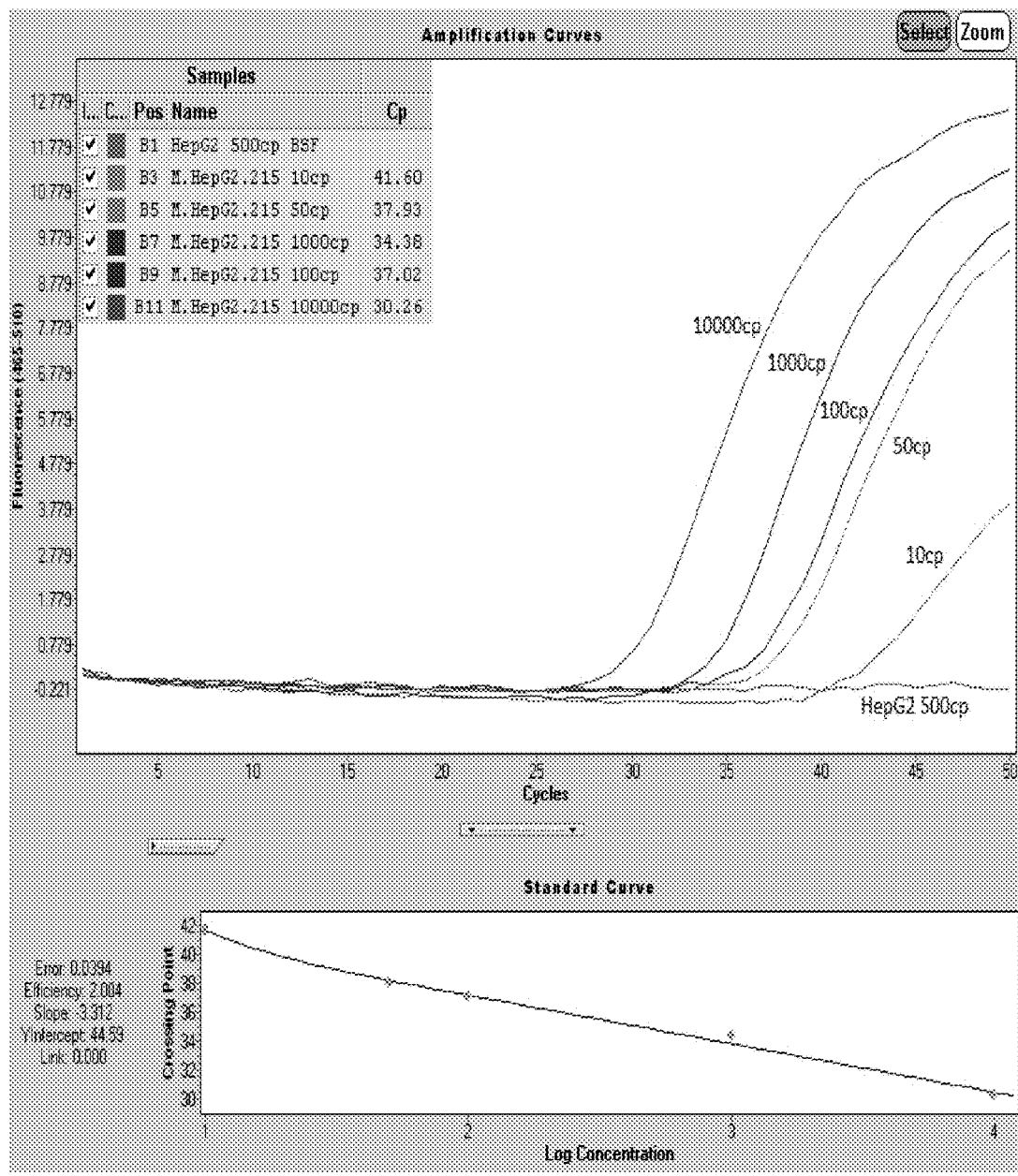
FIG. 8 shows results using the protocol for quantification of bisulfite converted CpG island 1 of the HBV genome.

Below is the detailed protocol for quantification of bisulfite converted CpG island 1 of the HBV genome (results shows in FIG. 8).

| Primer/Probe | Sequence: 5' to 3' | Product Size[1] |
|---|---|---|
| HBV_BSC1F1 (SEQ ID NO: 1) | GGTTTTTTTTGTTGATAAGAATTT | 79 bp |
| HBV_BSC1R3 (SEQ ID NO: 2) | CCCCCTAAAAAATTAAAAAAAA | |
| BSC1TQ (SEQ ID NO: 3) | [6FAM]TTATAATATTATAGAGTTTAGATTYGTGGTGGA[BHQ1] | |

Roche Light Cycler 480 - Template: Mono-color Hydrolysis Probe
95° C. 5 min, (95° C. 10 s 50° C. 15 s, 72° C. 10 s) × 50 cycles

| Component | [Stock] | [Final] | uL/rxn | DNA Template | HBV Copy/ul |
|---|---|---|---|---|---|
| LC480 Probe Master Mix | 2x | 1x | 5 | HepG2 BSF (500 copies) | 0 |
| HBV_BSC1_F1R3 | 10 uM | 1 uM | 1 | Meth. HepG2.215 | 10 |
| Probe (BSC1TQ) | 1 uM | 0.1 uM | 1 | Meth. HepG2.215 | 50 |
| H₂O | — | — | 2 | Meth. HepG2.215 | 100 |
| DNA Template | — | — | 1 | Meth. HepG2.215 | 1000 |
| | | Total: | 10 | Meth. HepG2.215 | 10000 |

Figure 9:
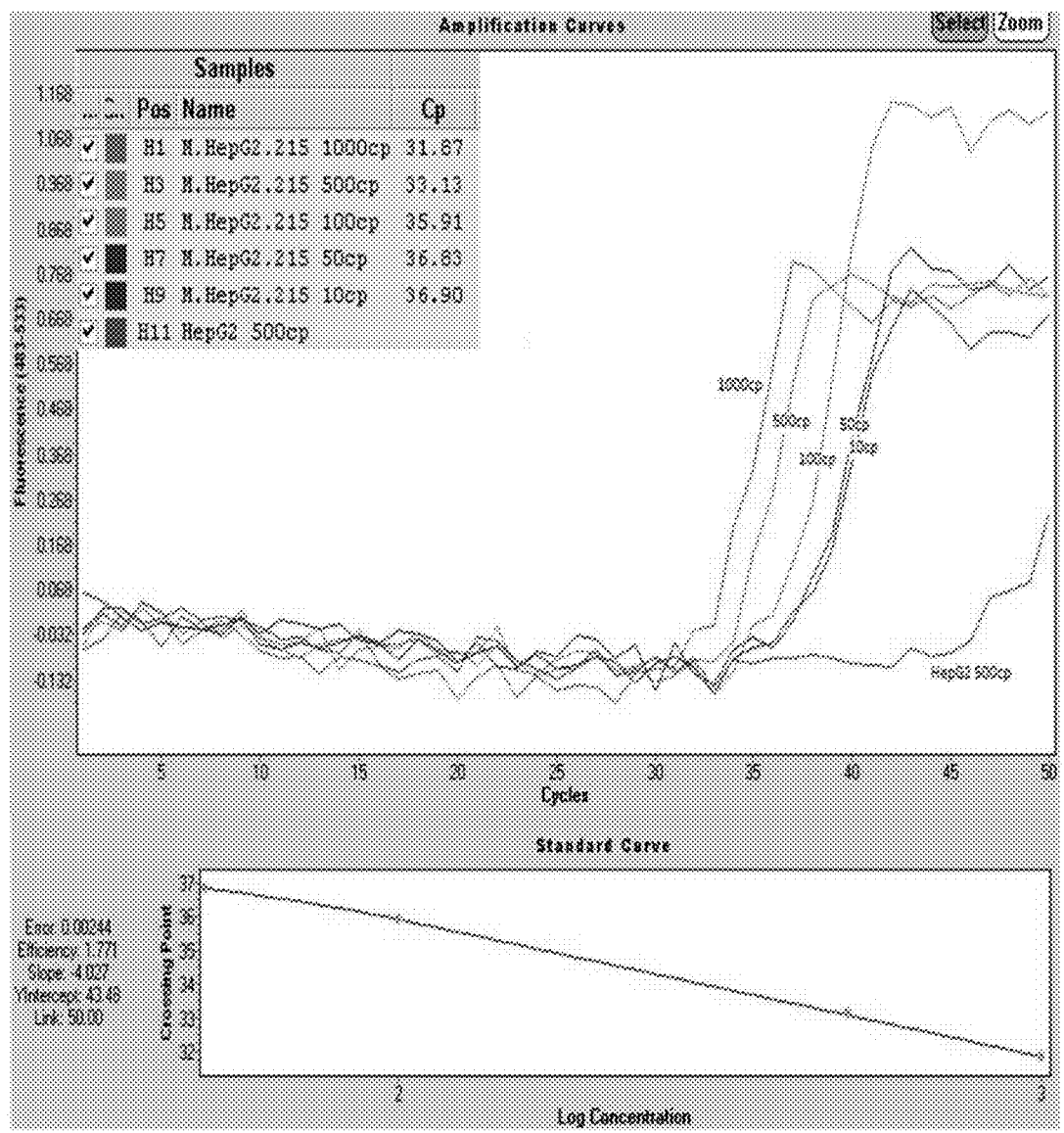
FIG. 9 shows results using the protocol for the quantification of methylated CpG island 1 of the HBV genome.

Below is the detailed protocol for the quantification of methylated CpG island 1 of the HBV genome (results shows in FIG. 9).

| Primer/Probe | Sequence: 5' to 3' | Product |
|---|---|---|
| HBV_C1F2B (SEQ ID NO: 4) | ACGTGTTTTGGTTAAAATTCGTAGTTTTTA | 110 bp |
| HBV_C1R5B (SEQ ID NO: 5) | AATATAATAAAACGCCGCAAACACATC | |
| C1MSTQ (SEQ ID NO: 6) | [6FAM]TTTTTTAATTTGTTTTGGTTATCGTTGGATG[BHQ1] | |

Roche Light Cycler 480 - Template: Mono-color Hydrolysis Probe
95° C. 5 min, (95° C. 10 s 55° C. 30 s, 72° C. 10 s) × 50 cycles

| Component | [Stock] | [Final] | uL/rxn | DNA Template | HBV copy/ul |
|---|---|---|---|---|---|
| LC480 Probe Master Mix | 2x | 1x | 5 | HepG2 BSF (500 copies) | 0 |
| HBV_C1F2B_R5B | 10 uM | 1 uM | 1 | Meth. HepG2.215 | 1 |
| Probe (C1MSTQ) | 1 uM | 0.1 uM | 1 | Meth. HepG2.215 | 5 |
| H₂O | — | — | 2 | Meth. HepG2.215 | 10 |
| DNA Template | — | — | 1 | Meth. HepG2.215 | 50 |
| | | Total: | 10 | Meth. HepG2.215 | 100 |
| | | | | Meth. HepG2.215 | 1000 |

45

Figure 10:
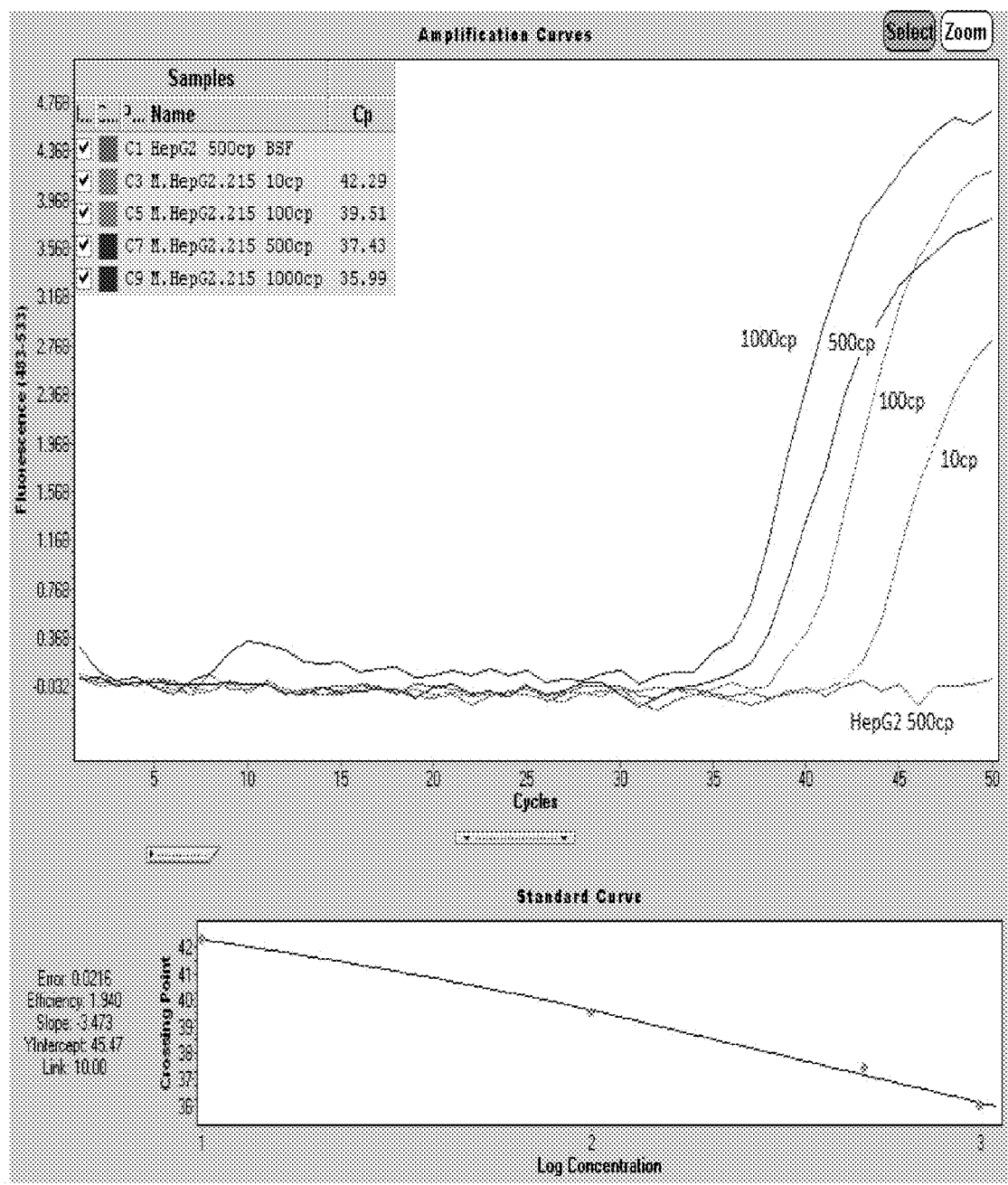
FIG. 10 shows results using the protocol for the quantification of bisulfite converted CpG island 2 of the HBV genome.

Below is the detailed protocol for the quantification of bisulfite converted CpG island 2 of the HBV genome (results shows in FIG. 10).

| Primer/Probe | Sequence: 5' to 3' | Product |
|---|---|---|
| HBV_BSC2F1 (SEQ ID NO: 7) | GGATTTTTGGATTTTTAGTAATGTT | 74 bp |
| HBV_BSC2R3 (SEQ ID NO: 8) | CCAATCTTTAAACAAACAATCTTTAA | |
| BSC2TQ (SEQ ID NO: 9) | [6FAM]ATGTTAAYGATYGATTTTGAGGTATATTTTAA[BHQ1] | |

Roche Light Cycler 480 - Template: Mono-color Hydrolysis Probe
95° C. 5 min, (95° C. 10 s 53° C. 15 s, 72° C. 10 s) × 50 cycles

| Component | [Stock] | [Final] | uL/rxn | DNA Template | HBV Copy/ul |
|---|---|---|---|---|---|
| LC480 Probe Master Mix | 2x | 1x | 5 | HepG2 BSF (500 copies) | 0 |
| HBV_BSC2_F1R3 | 10 uM | 1 uM | 1 | Meth. HepG2.215 | 10 |
| Probe (BSC2TQ) | 1 uM | 0.1 uM | 1 | Meth. HepG2.215 | 100 |
| H₂O | — | — | 2 | Meth. HepG2.215 | 500 |
| DNA Template | — | — | 1 | Meth. HepG2.215 | 1000 |
| | | Total: | 10 | | |

Figure 11:
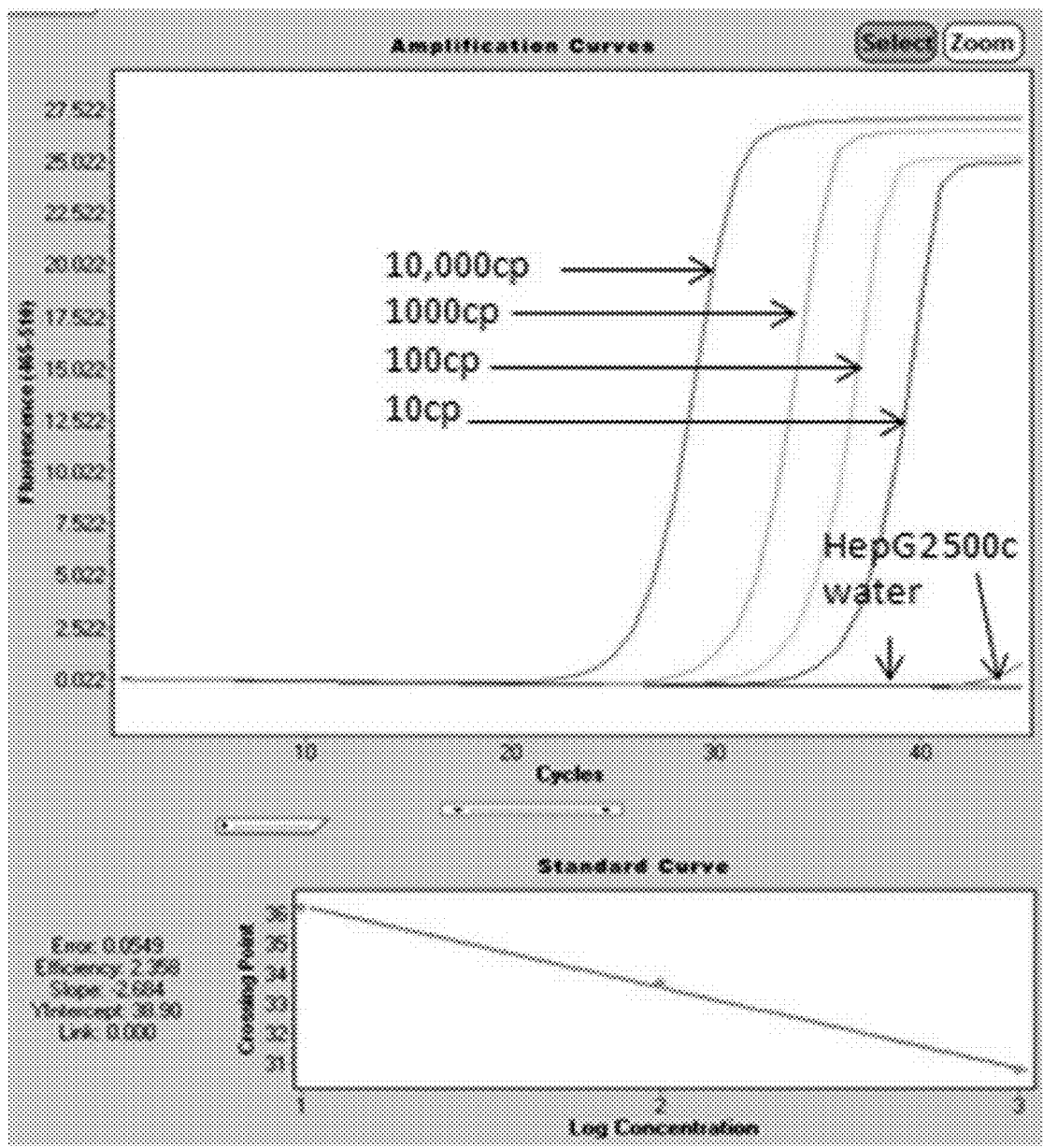
FIG. 11 shows results using the protocol for the quantification of methylated CpG island 2 of the HBV genome.
Figure 11:
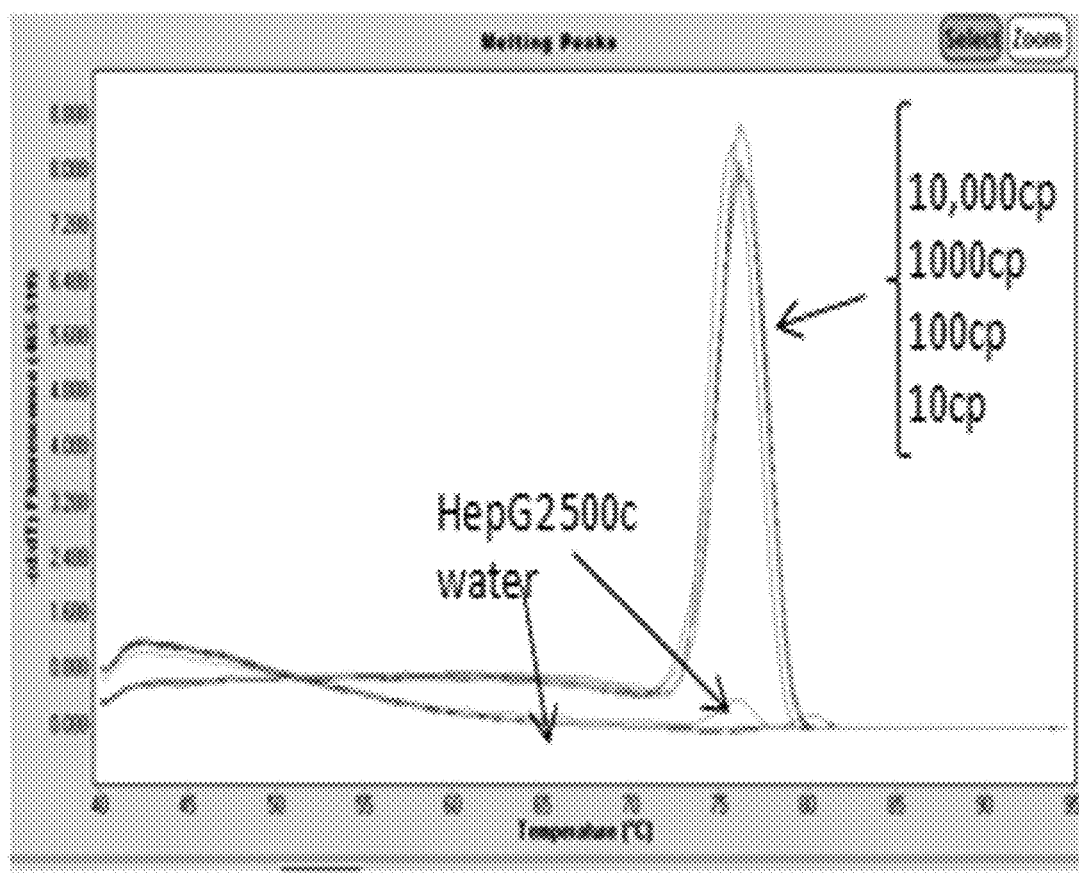

Below is the detailed protocol for the quantification of methylated CpG island 2 of the HBV genome (results shows in FIG. 11).

| Primer | Sequence: 5' to 3' | Product |
|---|---|---|
| HBV_C2MF3 (SEQ ID: 10) | TGTCGTTTCGGTCGATTAC | 78 bp |
| HBV_C2MR3 (SEQ ID NO: 11) | CACGATCCGACAAATAAAAA | |

Roche Light Cycler 480 - Template: SYBR Green I
95° C. 5 min, (95° C. 10 s 52° C. 30 s, 72° C. 10 s) × 45 cycles, Melting curve, 40° C. 30 S

| Component | [Stock] | [Final] | uL/reaction | DNA Template | HBV copy/ul |
|---|---|---|---|---|---|
| LC480 SYBR Green Mix | 2x | 1x | 5 | HepG2 BSF (500 copies) | 0 |
| HBV_C2MF3_R3 | 10 uM | 1 uM | 1 | Meth. HepG2.215 | 5 |
| H$_2$O | – | – | 3 | Meth. HepG2.215 | 10 |
| DNA Template | – | – | 1 | Meth. HepG2.215 | 100 |
| | | | | Meth. HepG2.215 | 1000 |
| | | Total: | 10 | Meth. HepG2.215 | 10000 |
| | | | | Meth. HepG2.215 | 20000 |

Figure 12:
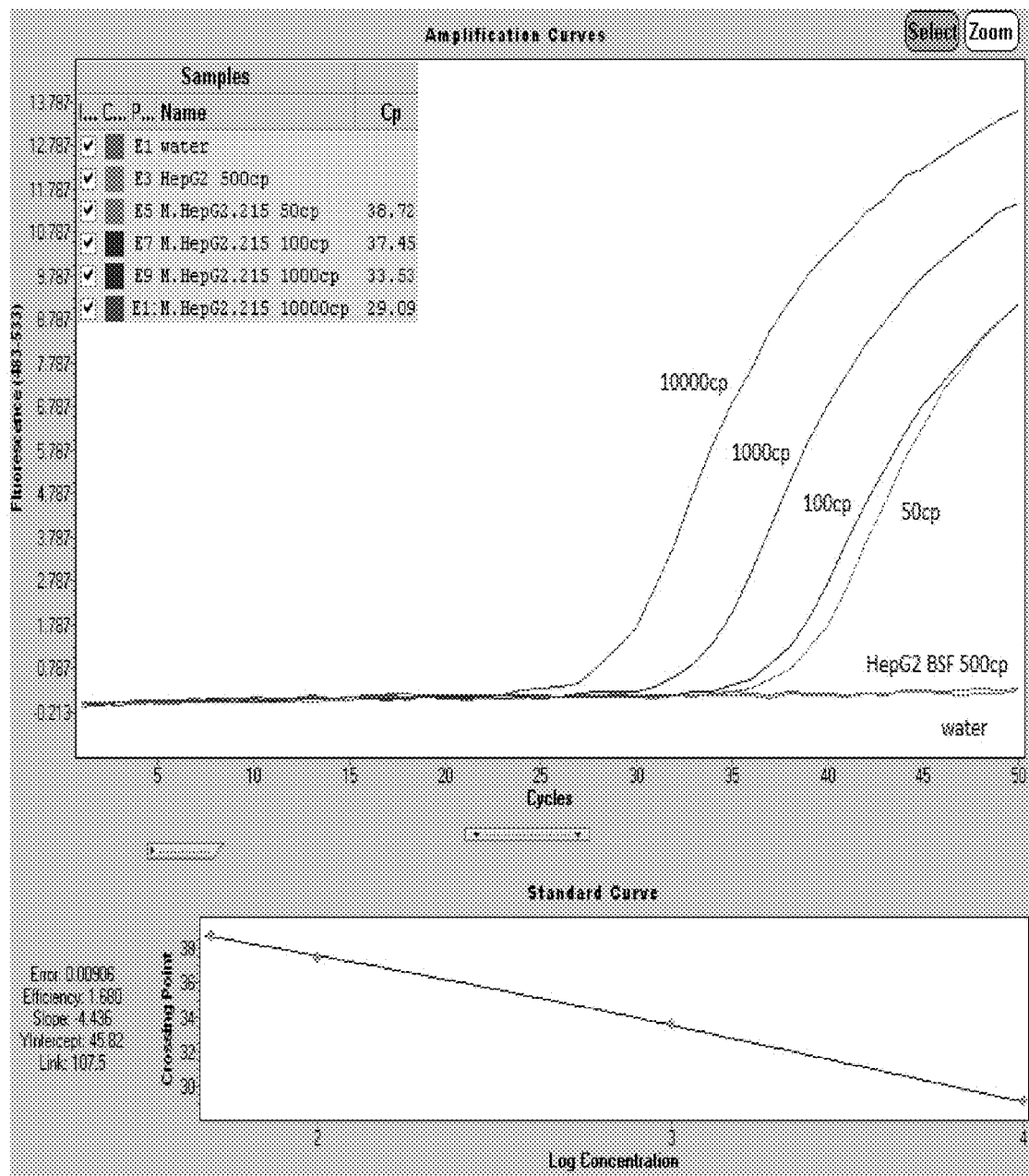
FIG. 12 shows results using the protocol for the quantification of bisulfite converted CpG island 3 of the HBV genome.

Below is the detailed protocol for the quantification of bisulfate converted CpG island 3 of the HBV genome (results shows in FIG. 12).

| Primer Name | Sequence: 5' to 3' | Product |
|---|---|---|
| HBV_BSC3F9 (SEQ ID NO: 12) | TTATGTTAATGTTAATATGGGTTTAAA | 79 bp |
| HBV_BSC3R9.10 (SEQ ID NO: 13) | TTCTCTTCCAAAAATAAAACAA | |
| C3BSTQ (SEQ ID NO: 14) | 6FAM-TTAgATAATTATTg+Tgg+T+T+T+TA+TA+T--BBQ | |

Roche Light Cycler 480 - Template: Mono Color Hydrolysis Probe I
95° C. 10 min, (95° C. 10 s, 52° C. 30 s, 72° C. 10 s) × 50 cycles

| Component | [Stock] | [Final] | uL/rxn | DNA Template | HBV copy/ul[1] |
|---|---|---|---|---|---|
| LC480 Probe Master Mix | 2x | 1x | 5 | water | 0 |
| HBV_BF9_R9.10 | 10 uM | 1 uM | 1 | HepG2 BSF (500 copies) | 0 |
| Probe (C3BSTQ) | 1 uM | 0.1 uM | 1 | Meth. HepG2.215 | 50 |
| H$_2$O | – | – | 2 | Meth. HepG2.215 | 100 |
| DNA Template | – | – | 1 | Meth. HepG2.215 | 1000 |
| | | Total: | 10 | Meth. HepG2.215 | 10000 |

Figure 13:
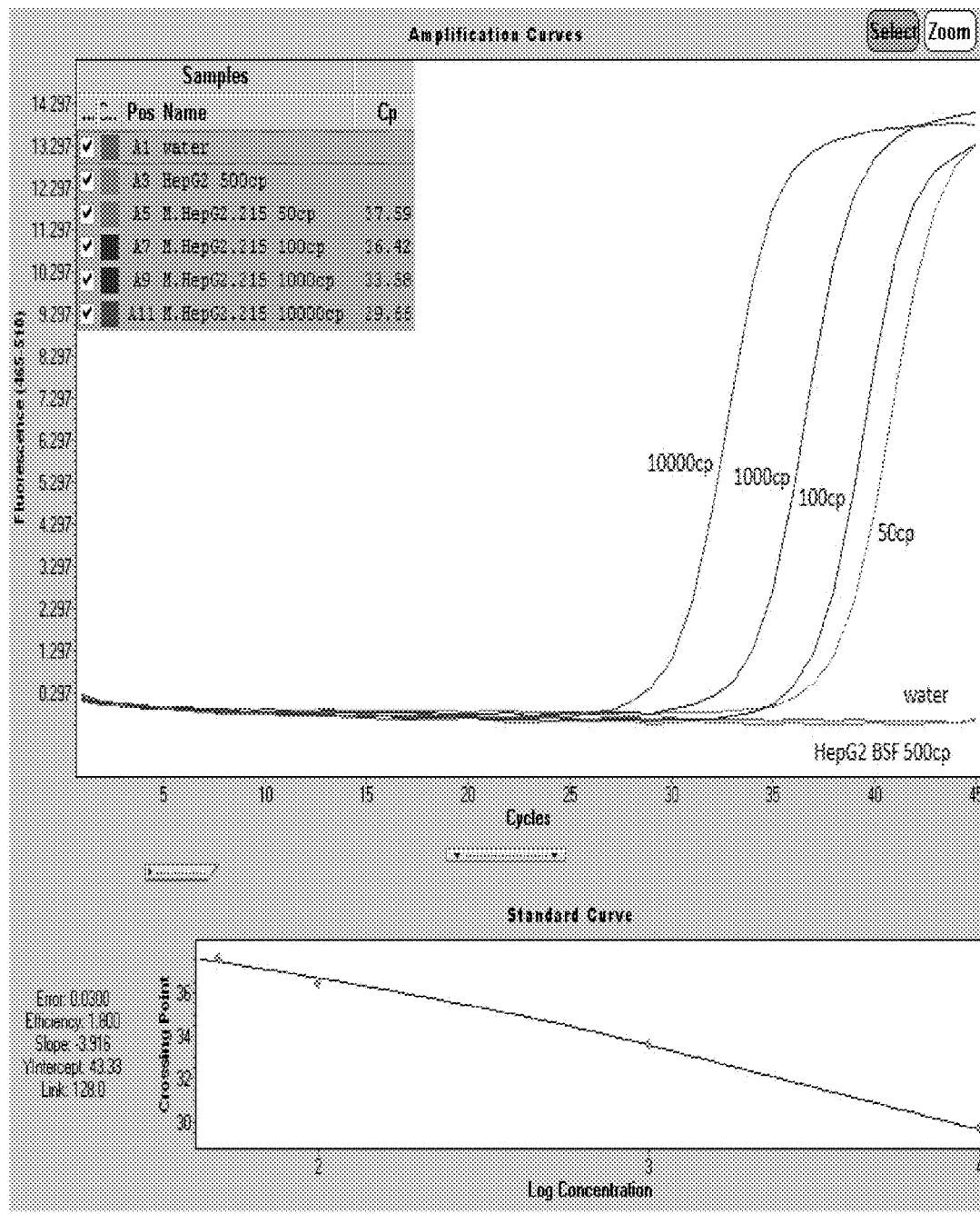
FIG. 13 shows results using the protocol for the quantification of methylated CpG island 3 of the HBV genome.

Below is the detailed protocol for the quantification of methylated CpG island 3 of the HBV genome (results shows in FIG. 13).

| Primer Name | Sequence: 5' to 3' | Product |
|---|---|---|
| HBV_MSP2F (SEQ ID NO: 15) | GTGTGGATTCGTATTTTTTC | 143 bp |
| HBV_MSP2R (SEQ ID NO: 16) | GACGATTAAAACCTTCGTCT | |
| C3AMSTQ (SEQ ID NO: 17) | AACCTACCTCGTCGTCTAACAACAAT | |

Roche Light Cycler 480 - Template: Mono Color Hydrolysis Probe I
95° C. 10 min, (95° C. 10 s, 53° C. 30 s, 72° C. 10 s) × 45 cycles

| Component | [Stock] | [Final] | uL/rxn | DNA Template | HBV Copy/ul |
|---|---|---|---|---|---|
| LC480 Probe Master Mix | 2x | 1x | 5 | water | 0 |
| HBV_MSP2F_2R | 10 uM | 1 uM | 1 | HepG2 BSF (500 copies) | 0 |
| Probe (C3AMSTQ) | 1 uM | 0.1 uM | 1 | Meth. HepG2.215 | 50 |
| H$_2$O | – | – | 2 | Meth. HepG2.215 | 100 |
| DNA Template | – | – | 1 | Meth. HepG2.215 | 1000 |
| | | Total: | 10 | Meth. HepG2.215 | 10000 |

Figure 14:
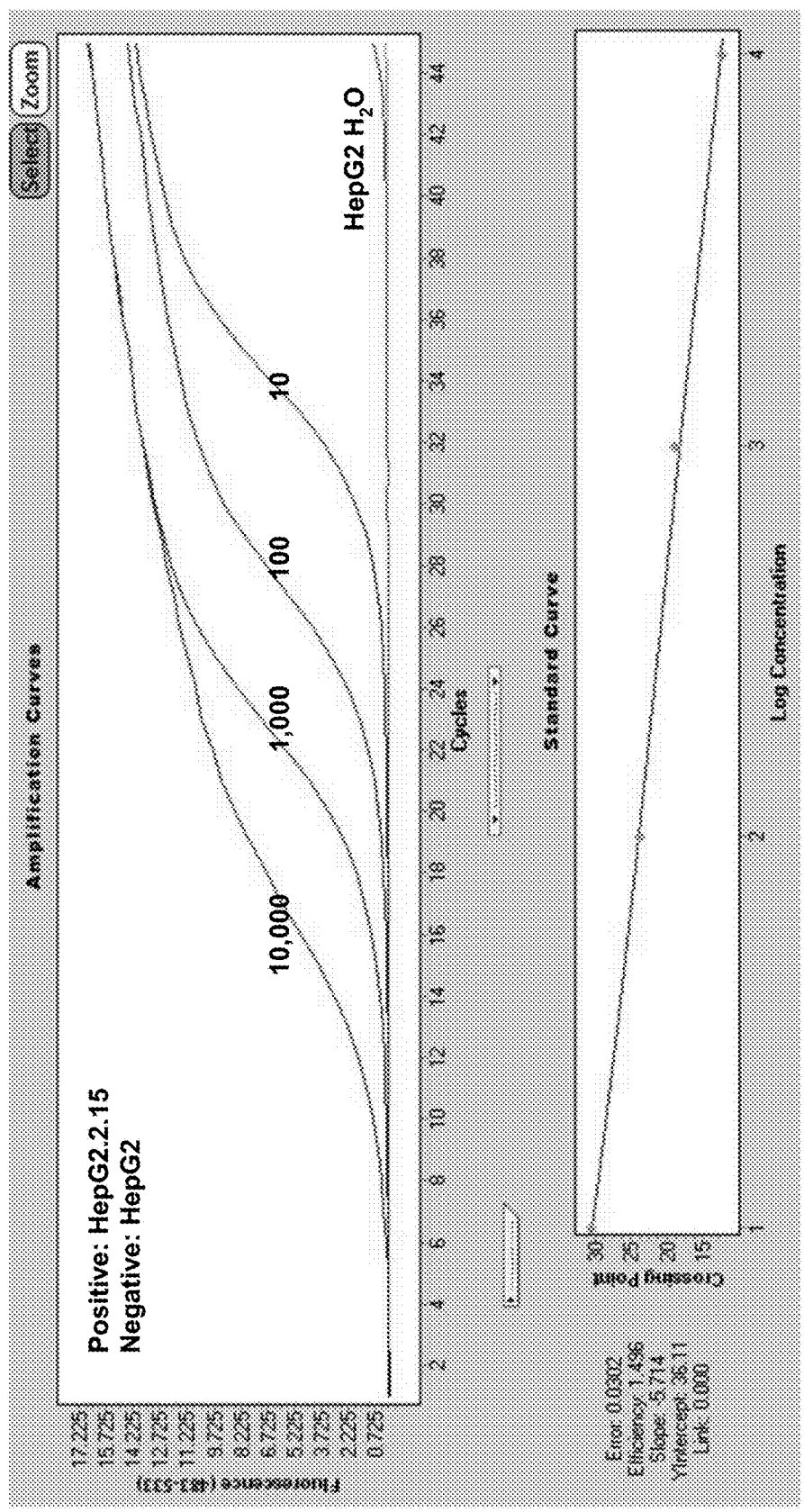
FIG. 14 shows results using the protocol for detection of circulation derived methylated CpG island 3 of the HBV genome by using HBV-MSP Short Amplicon Assay (mHBV).

Below is the detailed protocol for detection of circulation derived methylated CpG island 3 of the HBV genome by using HBV-MSP Short Amplicon Assay (mHBV) Target Amplicon Size: 42 bp (results shows in FIG. 14).

| Primer Name | Sequence: 5' to 3' | Product |
|---|---|---|
| HBV_SMF1 (SEQ ID NO: 18) | GCTCTTCGTGGTGTGGTGAAGAAGAATTTTTTCGTTTC | 42 bp |
| HBV_MSP2R (SEQ ID NO: 16) | GACGATTAAAACCTTCGTCT | |
| HBV_S2F1 (SEQ ID NO: 19) | TGTGGTGAAGAAGAATT | |
| HBV_S2R1 (SEQ ID NO: 20) | GACGATTAAAACCTTC | |

1st PCR: Product size - 60 bp

| Component | Stock Concentration | Final Concentration | uL/reaction |
|---|---|---|---|
| 10X PCR Buffer | 10X | 1X | 1 |
| dNTP | 2.5 mM each | 250 uM each | 0.8 |
| HBT_SMF1/MSP2R | 10 uM | 1 uM | 1 |
| HotStart Taq Plus | 5 U/uL | 1 U/reaction | 0.2 |
| DNA Template | — | — | 1 |
| H₂O | — | — | 6 |
| Total | | | 10 |

Eppendorf Thermal Cycler: 95° C. 5 min, (95° C. 30 s, 50° C. 30 s, 72° C. 30 s) x 27 cycles, 72° C. 4 min, 4° C. Hold
*Dilute 1st PCR products 1:10 by adding 90 uL H₂O to each tube.

2nd PCR: Product size - 45 bp

| Component | Stock Concentration | Final Concentration | uL/reaction |
|---|---|---|---|
| LC480 SYBR Green Mix | 2X | 1X | 5 |
| HBV_S2F1/R1 | 10 uM | 1 uM | 1 |
| 1st PCR Product (1:10) | — | — | 1 |
| H₂O | — | — | 3 |
| Total | | | 10 |

Figure 15:
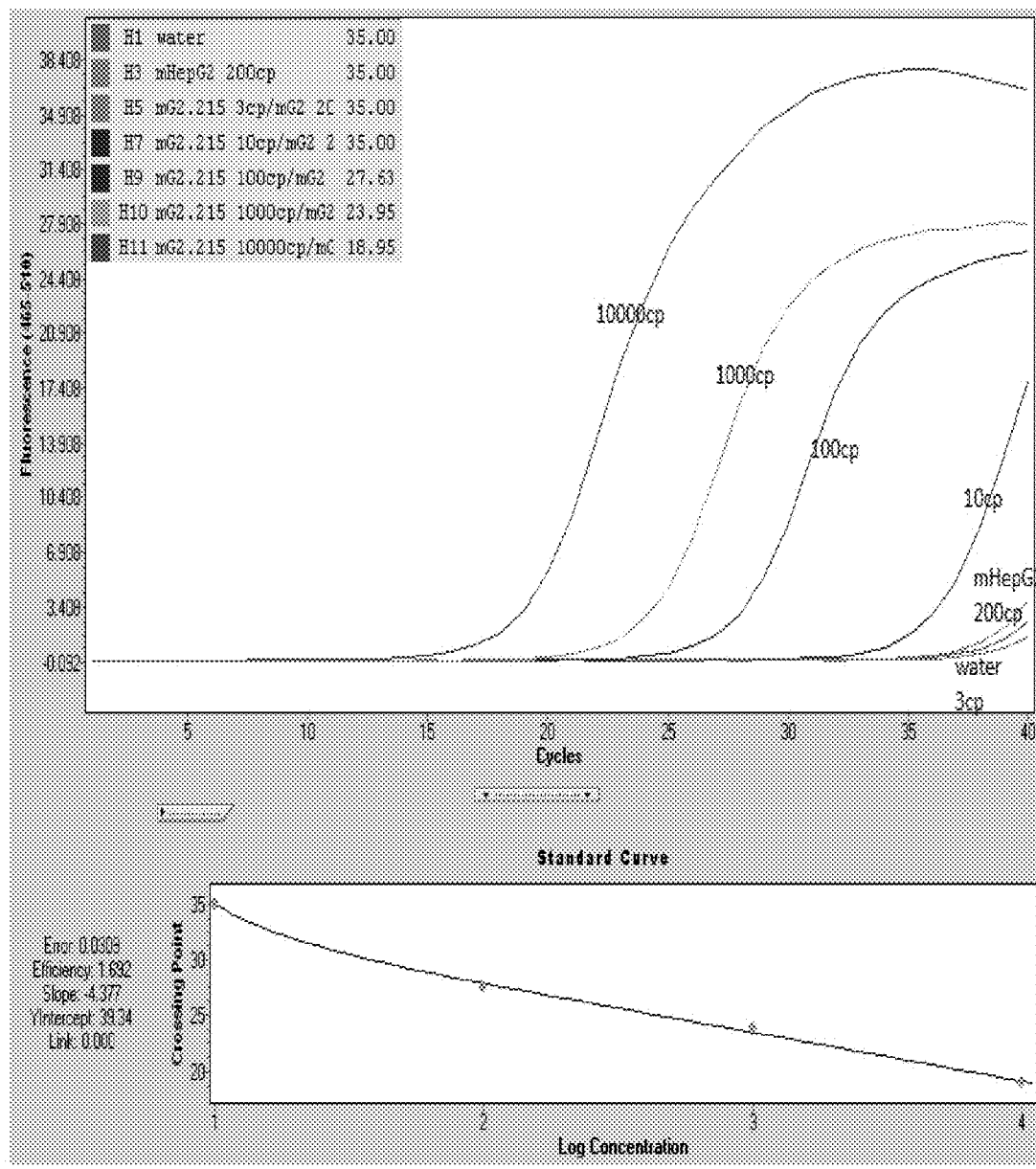
FIG. 15 shows results using the protocol for quantification of methylated CpG island 3 of the HBV genome by a short amplicon MSP assay that can be used for fragmented DNA.
Figure 15:
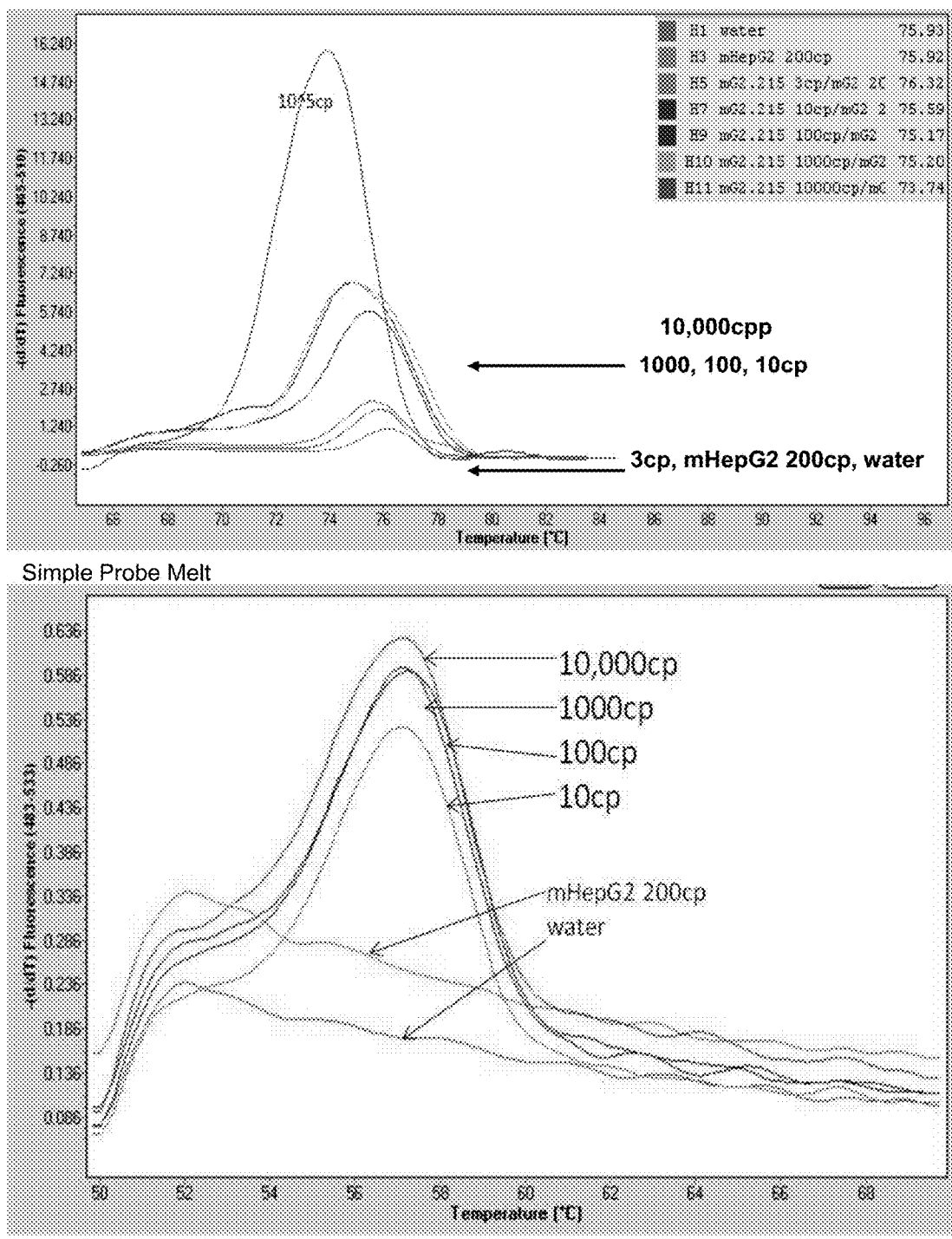

Roche LightCycler 480 - Template: SYBR Green I
95° C. 5 min, (95° C. 10 s, 50° C. 15 s, 72° C. 10 s) x 45 cycles, Melting curve, 40° C. 30 s Below is the detailed protocol for quantification of methylated CpG island 3 of the HBV genome by a short amplicon MSP assay that can be used for fragmented DNA (results shows in FIG. 15).

| Primer Name | Sequence: 5' to 3' | Product |
|---|---|---|
| C3.M_F1 (SEQ ID NO: 21) | AGAATTTTTTCGTTTCGTAGAC | 55 bp |
| C3.M_R3 (SEQ ID NO: 22) | AAAATCTTCTACGACGCGACGATTAA | |
| C3.M_R2 (SEQ ID NO: 23) | CTACGACGCGACGATTAAAAC | |
| CG3.MSP SP (SEQ ID NO: 24) | FLQ-TCgTTTCgTAgACgAAggT--PH | |

First Step:
Hotstart TAQ Plus Amplification: Eppendorf Vapo Protect Thermocycler - Program Template: Hotstart 95° C. 5 min, (95° C. 30 s, 50° C. 30 s, 72° C. 30 s) x 27 Pause + 40 cycles; 72° C. 4 min, 4° C. hold
After 27 cycles, take out 1 uL and dilute with 9 ul H2O (2nd step template), put back remaining reaction volume for 40 cycles (melt template)
Second step:
Roche Light Cycler 480 - Template: SybrGreen
95° C. 5 min, (95° C. 10 s, 53° C. 30 s, 72° C. 10 s) x 45 cycles
Melt step:
Roche Light Cycler 480 - Template: Simple Probe
95° C. 1 min, 95° C. 60 s, 40° C. 120 s, 95° C. continuous; 40° C. 30 s

| Hotstart TAQ Plus Amplification | | | | | |
|---|---|---|---|---|---|
| Component | [Stock] | [Final] | uL/rxn | DNA Template BSF | HBV Copy/ul |
| HotStart TAQ Plus | 2x | 1x | 5 | water | 0 |
| C3.M_F1/R3 | 10 uM | 1 uM | 1 | Meth. HepG2 (200 copies) | 0 |
| H$_2$O | — | — | 1 | Meth. HepG2.215* | 3 |
| DNA Template | — | — | 1 | Meth. HepG2.215* | 10 |
| | | Total: | 10 | Meth. HepG2.215* | 100 |
| | | | | Meth. HepG2.215* | 1000 |
| | | | | Meth. HepG2.215* | 10000 |

*In background of Meth. HepG2 200 cp

| Sybrgreen qPCR (2nd step) | | | | Simple Probe Melt | | | |
|---|---|---|---|---|---|---|---|
| Component | [Stock] | [Final] | uL/rxn | Component | [Stock] | [Final] | uL/rxn |
| LC480 Sybrgreen Master | 2x | 1x | 5 | CG3.MSP SP | 2 uM | 0.2 uM | 1 |
| C3.M_F1/R2 | 10 uM | 1 uM | 1 | H$_2$O | — | — | 5 |
| H$_2$O | — | — | 1 | DNA Template (Hotstart TAQ amplification PCR product) | — | — | 4 |
| DNA Template | — | — | 1 | | | | |
| | | Total: | 10 | | | | |
| | | | | | | Total: | 10 |

Figure 16:
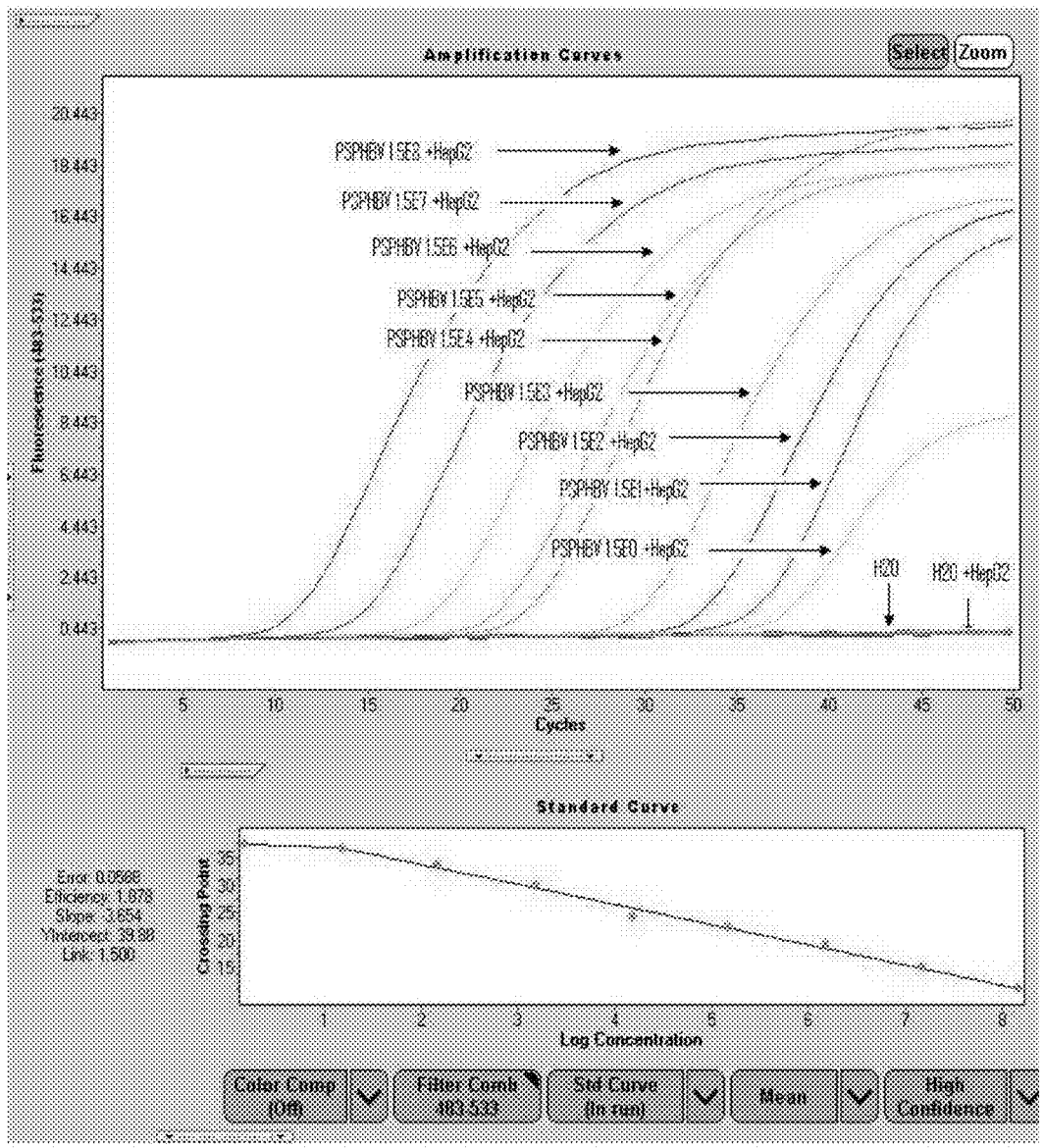
FIG. 16 shows results using the protocol for quantification of genomic CpG island 1 of the HBV genome.

Below is the detailed protocol for quantification of genomic CpG island 1 of the HBV genome (results shows in FIG. 16).

| Primer/Probe | Sequence: 5' to 3' | Product Size |
|---|---|---|
| HBV240F3 (SEQ ID NO: 25) | GTCTAGACTCGTGGTGGA | 64 bp |
| HBVC240R1 (SEQ ID NO: 26) | TTTTGGCCAGGACAC | |
| HBV240 TaqMan (SEQ ID NO: 27) | [6FAM]CAATTTTCTAGGGGGAGCACCCAC[BHQ1] | |

Roche Light Cycler 480 - Template: Mono-color Hydrolysis Probe
95° C. 5 min, (95° C. 10 s 54° C. 10 s, 64° C. 15 s) x 45 cycles

| Component | [Stock] | [Final] | uL/rxn | DNA Template | HBV Copy/ul |
|---|---|---|---|---|---|
| LC480 Probe Master Mix | 2x | 1x | 5 | PSP65 HBV + HepG2 0.1 ng/ul | 1.5E8 |
| HBV240F3/C240R1 | 10 uM | .5 uM | 0.5 | PSP65 HBV + HepG2 0.1 ng/ul | 1.5E7 |
| Probe (HBV240 TaqMan) | 3 uM | 0.15 uM | 0.5 | PSP65 HBV + HepG2 0.1 ng/ul | 1.5E6 |
| H$_2$O | — | — | 2 | PSP65 HBV + HepG2 0.1 ng/ul | 1.5E5 |
| DNA Template | — | — | 1 | PSP65 HBV + HepG2 0.1 ng/ul | 1.5E4 |
| | | Total: | 10 | PSP65 HBV + HepG2 0.1 ng/ul | 1.5E3 |
| | | | | PSP65 HBV + HepG2 0.1 ng/ul | 1.5E2 |
| | | | | PSP65 HBV + HepG2 0.1 ng/ul | 1.5E1 |
| | | | | PSP65 HBV + HepG2 0.1 ng/ul | 1.5 |
| | | | | H2O + HepG2 | |

Figure 17:
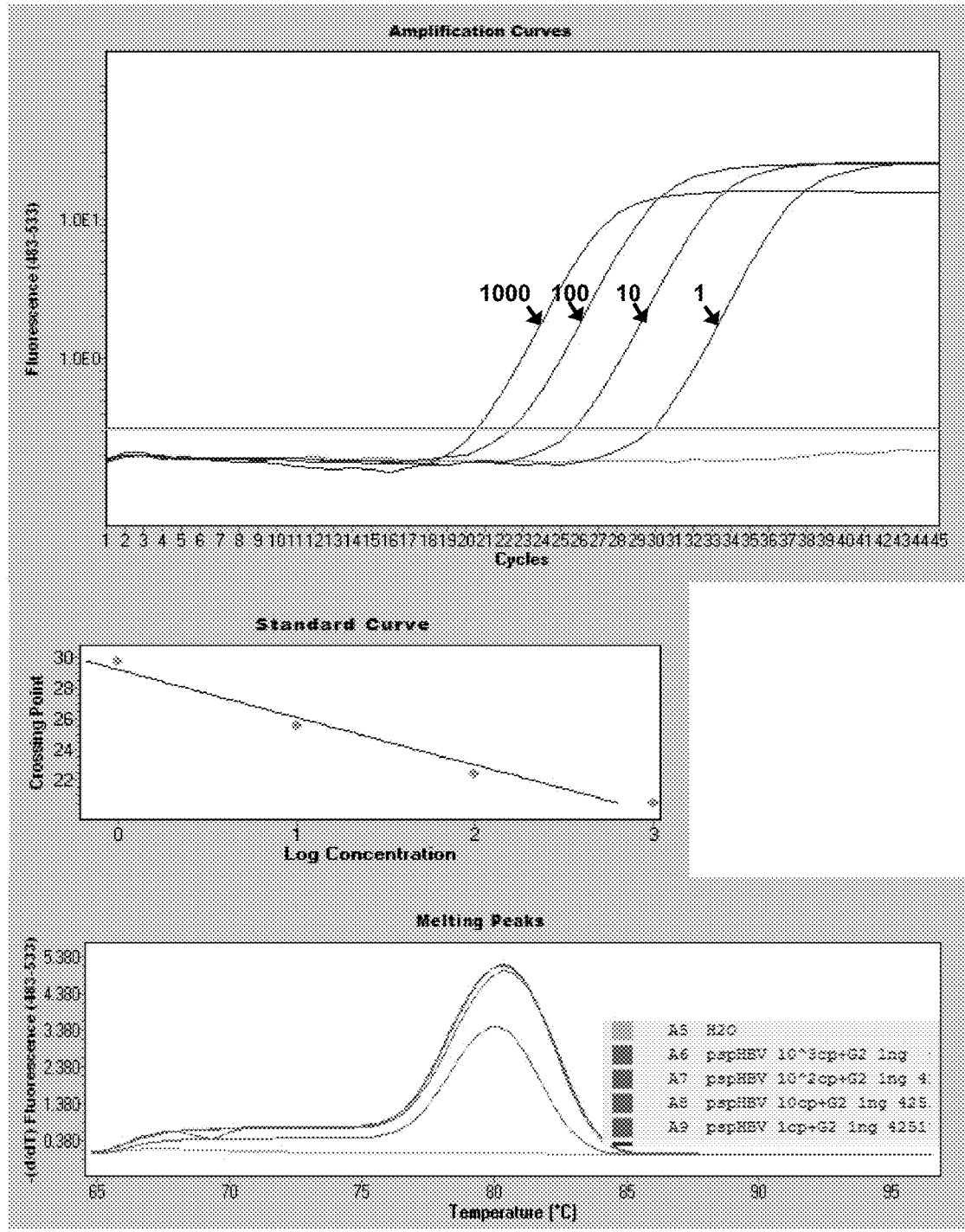
FIG. 17 shows results using the protocol for quantification of genomic CpG island 2 of the HBV genome.

Below is the detailed protocol for quantification of genomic CpG island 2 of the HBV genome (results shows in FIG. 17).

| Primer/Probe | Sequence: 5' to 3' | Product Size |
|---|---|---|
| HBV_F_1583_1602 (SEQ ID NO: 28) | ACTTCGCTTCACCTCTGCAC | 39 bp |
| HBV_R_1604_1622 (SEQ ID NO: 29) | CACGGTGGTCTCCATGCTAC | |

Roche Light Cycler 480 - Template: SYBR Green
95° C. 5 min, (95° C. 10 s 60° C. 10 s, 72° C. 10 s) x 45 cycles, melt [95° C. 5 s, 65° C. 60 s, 97° C. continuous, 40 C. 30 s

| Component | [Stock] | [Final] | uL/rxn | DNA Template | HBV Copy/ul |
|---|---|---|---|---|---|
| LC480 SYBR Green | 2x | 1x | 5 | pspHBV 1000 cp + HepG2 1 ng | 1000 |
| HBV | 10 uM | 1 uM | 1 | pspHBV 100 cp + HepG2 1 ng | 100 |
| F1583_1603/R_1604_1622 | | | | pspHBV 10 cp + HepG2 1 ng | 10 |
| H₂O | — | — | 3 | pspHBV 1 cp + HepG2 1 ng | 1 |
| DNA Template | — | — | 1 | H2O | |
| | | Total: | 10 | | |

Figure 18:
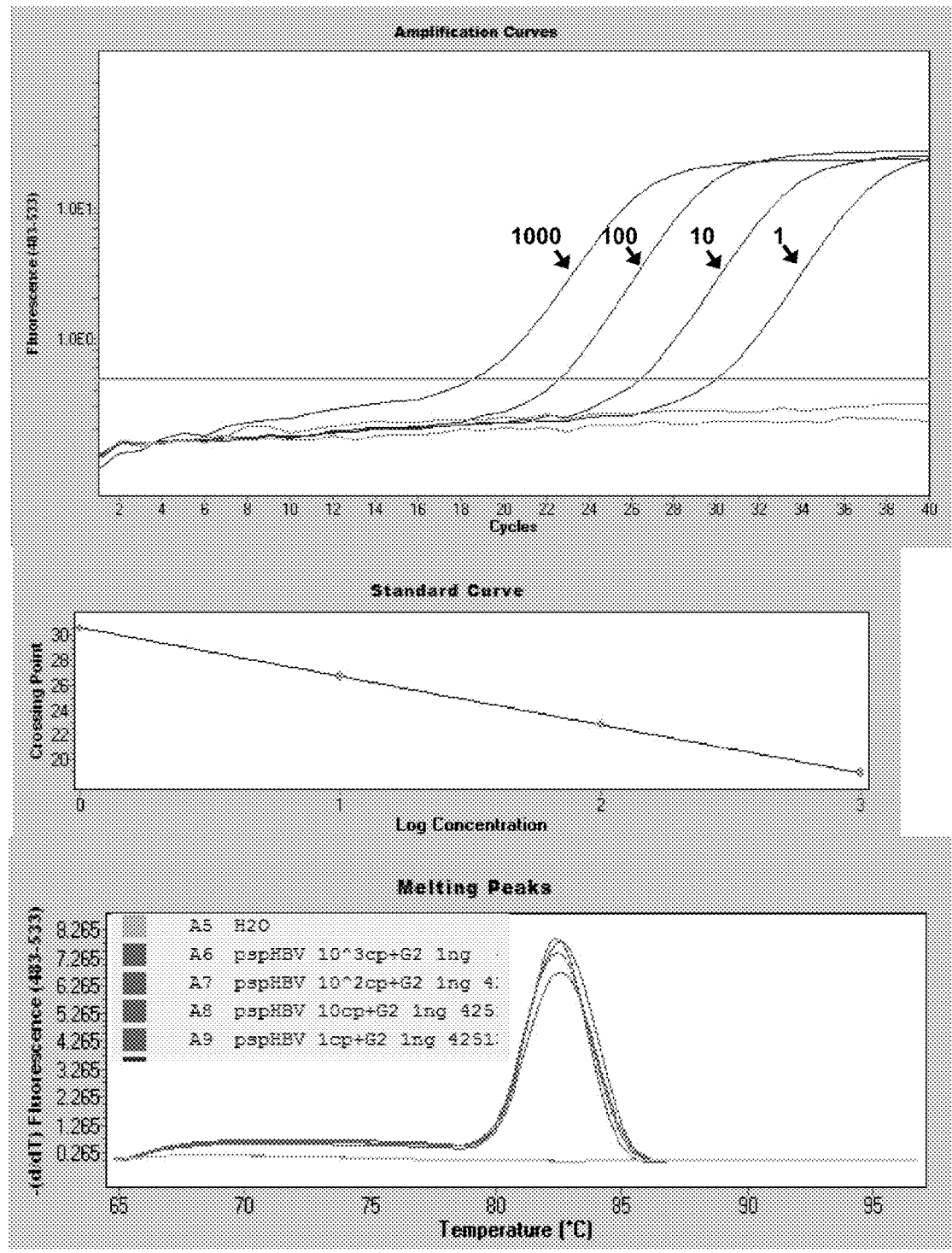
FIG. 18 shows results using the protocol for quantification of genomic CpG island 2 of the HBV genome.

Below is the detailed protocol for quantification of genomic CpG island 2 of the HBV genome (results shows in FIG. 18).

| Primer/Probe | Sequence: 5' to 3' | Product Size |
|---|---|---|
| HBV_F_1613_1629 (SEQ ID NO: 30) | GACCACCGTGAACGCCC | 58 bp |
| HBVRev1671_1654_Chr21 (SEQ ID NO: 31) | AGTCCAAGAGTCCTGTTGTGCAAGACCTT | |

Roche Light Cycler 480 - Template: SYBR Green
95° C. 5 min, (95° C. 10 s 60° C. 10 s, 72° C. 10 s) × 45 cycles, melt [95° C. 5 s, 65° C. 60 s, 97° C. continuous], 40 C. 30 s

| Component | [Stock] | [Final] | uL/rxn | DNA Template | HBV Copy/ul |
|---|---|---|---|---|---|
| LC480 SYBR Green | 2x | 1x | 5 | pspHBV 1000 cp + HepG2 1 ng | 1000 |
| HBV_F_1613_1629/ | 10 uM | 1 uM | 1 | pspHBV 100 cp + HepG2 1 ng | 100 |
| HBVRev1671_1654_Chr21 | | | | pspHBV 10 cp + HepG2 1 ng | 10 |
| H₂O | — | — | 3 | pspHBV 1 cp + HepG2 1 ng | 1 |
| DNA Template | — | — | 1 | H2O | |
| | | Total: | 10 | | |

Figure 19:
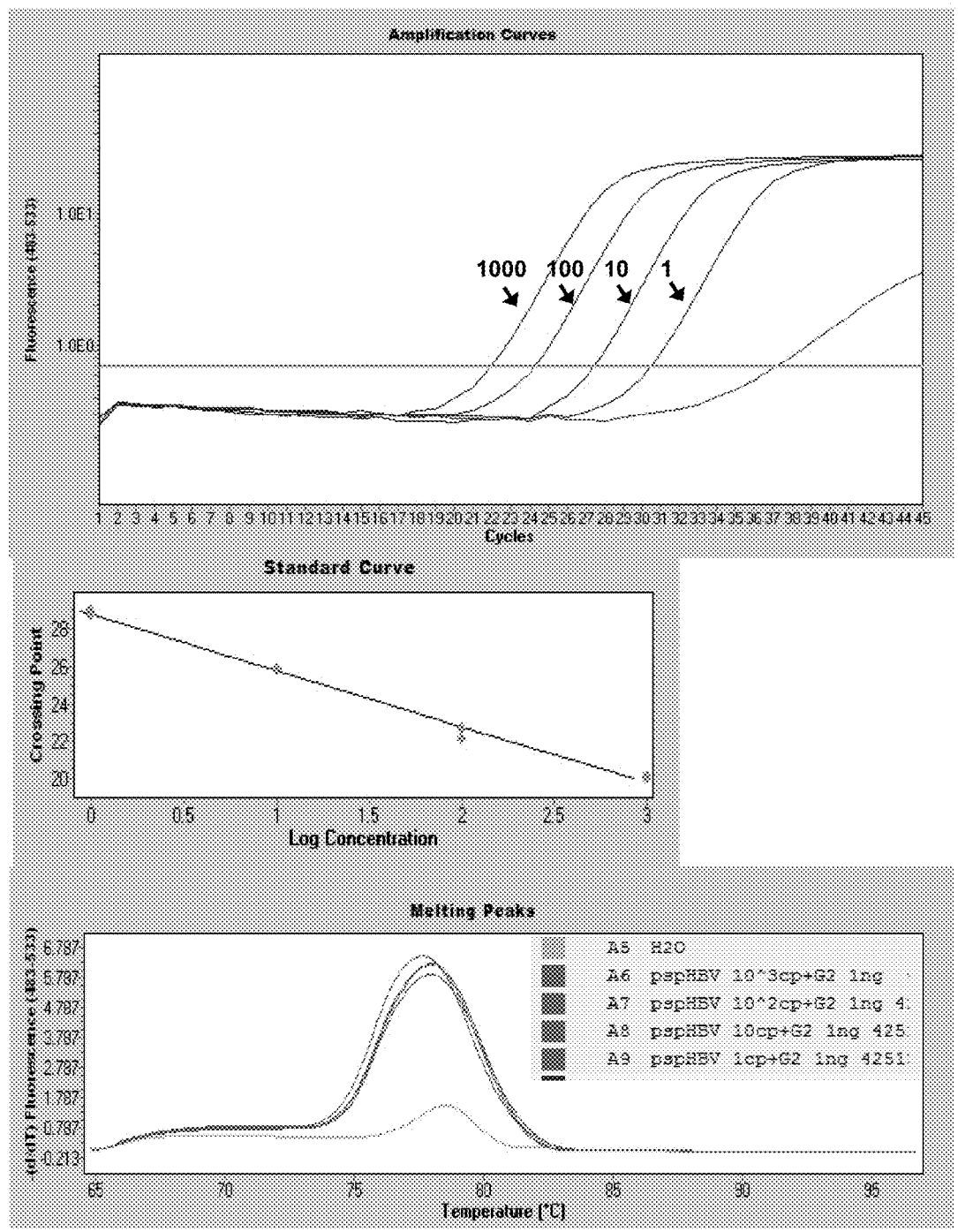
FIG. 19 shows results using the protocol for quantification of genomic CpG island 2 of the HBV genome.

Below is the detailed protocol for quantification of genomic CpG island 2 of the HBV genome (results shows in FIG. 19).

| Primers | Sequence: 5' to 3' | Product Size |
|---|---|---|
| HBV_F_1633_1653 (SEQ ID NO: 32) | AGGTCTTGCCCAAGGTCTTAC | 47 bp |
| HBV_R_1660_1680 (SEQ ID NO: 33) | TTGCTGAGAGTCCAAGAGTCC | |

Roche Light Cycler 480 - Template: SYBR Green
95° C. 5 min, (95° C. 10 s 60° C. 10 s, 72° C. 10 s) × 45 cycles, melt [95° C. 5 s, 65° C. 60 s, 97° C. continuous], 40 C. 30 s

| Component | [Stock] | [Final] | uL/rxn | DNA Template | HBV Copy/ul |
|---|---|---|---|---|---|
| LC480 SYBR Green | 2x | 1x | 5 | pspHBV 1000 cp + HepG2 1 1 ng | 1000 |
| HBV | 10 uM | 1 uM | 1 | pspHBV 100 cp + HepG2 1 ng | 100 |
| F1633_1653/R_1660_1680 | | | | | |
| H₂O | — | — | 3 | pspHBV 10 cp + HepG2 1 ng | 10 |
| DNA Template | — | — | 1 | pspHBV 1 cp + HepG2 1 ng | 1 |
| | | Total: | 10 | H2O | |

Figure 20:
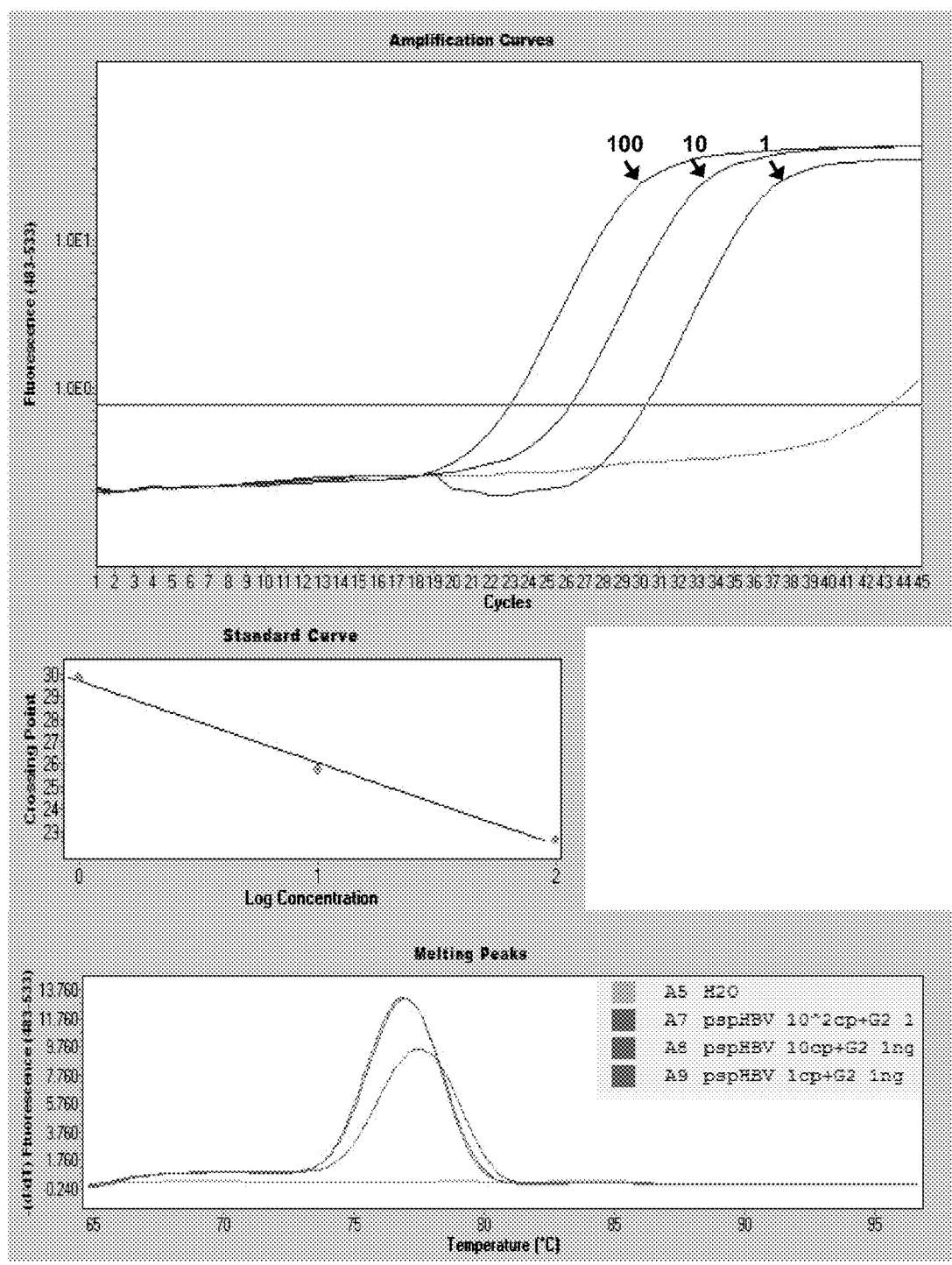
FIG. 20 shows results using the protocol for quantification of genomic CpG island 2 of the HBV genome.

Below is the detailed protocol for quantification of genomic CpG island 2 of the HBV genome (results shows in FIG. 20).

| Primer/Probe | Sequence: 5' to 3' | Product Size |
|---|---|---|
| HBV_F_1685_1719 (SEQ ID NO: 34) | AACGACCGACCTTGAGGCATACTTC | 55 bp |
| HBV_R_1713_1740 (SEQ ID NO: 35) | CTCCTCCCAGTCTTTAAACAAACAGTC | |

-continued

```
Roche Light Cycler 480 - Template: SYBR Green
95° C. 5 min, (95° C. 10 s 60° C. 10 s, 72° C. 10 s) x 45 cycles,
melt [95° C. 5 s, 65° C. 60 s, 97° C. continuous], 40 C. 30 s
                                         uL/                         HBV
Component                  [Stock] [Final] rxn DNA Template         Copy/ul LC480 SYBR Green             2x     1x     5  pspHBV 100 cp + HepG2 1 ng   100
HBV_F_1685_1719/R_1713_1740  10 uM  1 uM   1  pspHBV 10 cp + HepG2 1 ng    10
H2O                          —      —      3  pspHBV 1 cp + HepG2 1 ng    1
DNA Template                 —      —      1  H2O Total:   10
```

Figure 21:
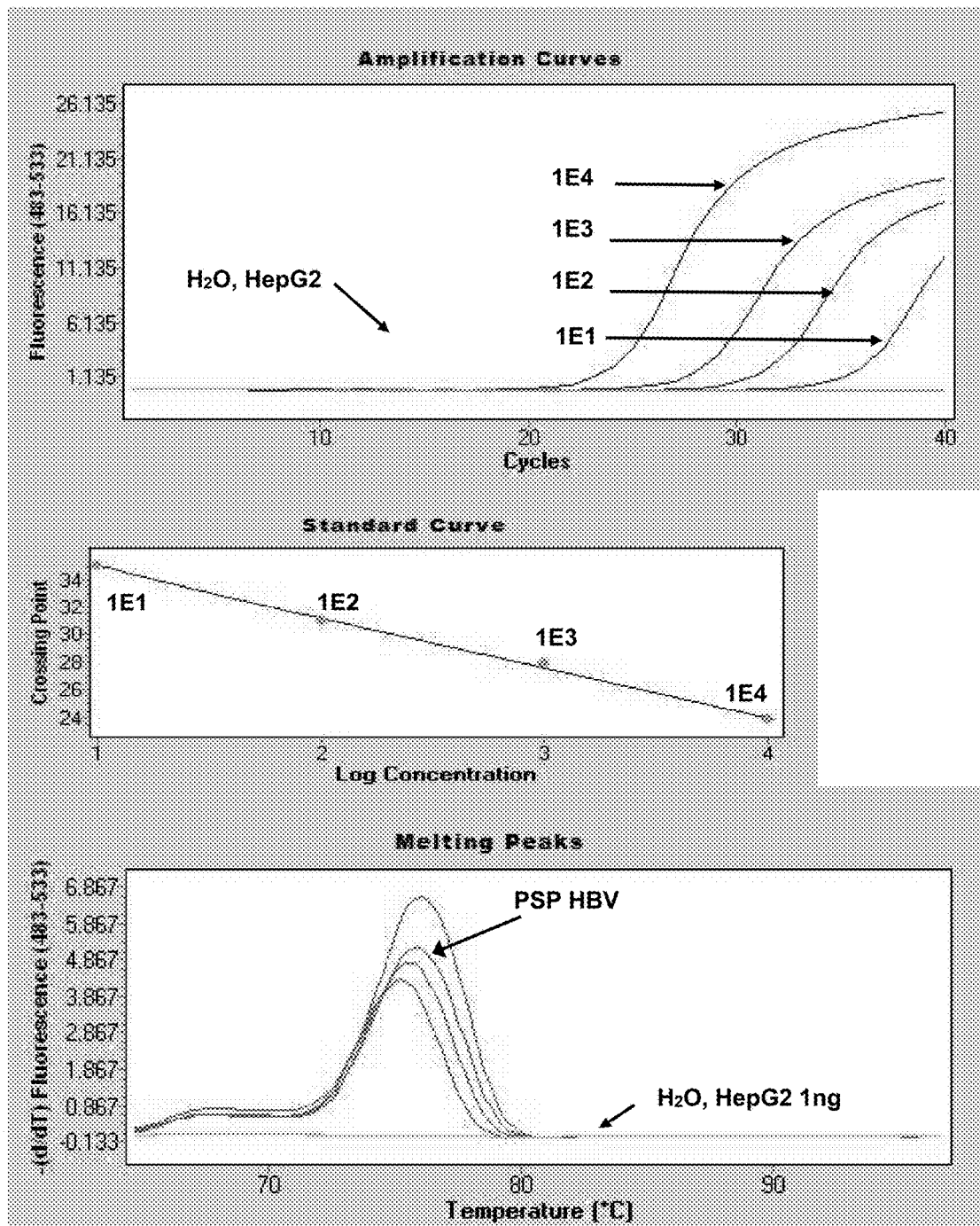
FIG. 21 shows results using the protocol for quantification of genomic CpG island 2 of the HBV genome.

Below is the detailed protocol for quantification of genomic CpG island 2 of the HBV genome (results shows in FIG. 21).

```
Primer/Probe                    Sequence: 5' to 3'                Product Size HBV_F_1741_1767 (SEQ ID NO: 36)  TRGGGGAGGAGATAAGGTTAAAGGTC       50 bp

HBV_R_1768_1791 SEQ ID NO: 37)   ATGCCTACAGCCTCCTAGTACAA
```

```
Roche Light Cycler 480 - Template: SYBR Green
95° C. 5 min, (95° C. 10 s 65° C. 10 s, 72° C. 8 s) x 40 cycles,
melt [95° C. 5 s, 65° C. 60 s, 97° C. continuous], 40 C. 30 s
                                         uL/
Component                  [Stock] [Final] rxn DNA Template          HBV Copy/ul LC480 Sybrgreen Master       2x     1x     5  PSP65 HBV + HepG2 1 ng/ul   1.0E4
HBV_F_1741_1767/R_1768_1791  10 uM  1 uM   1  PSP65 HBV + HepG2 1 ng/ul   1.0E3
H2O                          —      —      3  PSP65 HBV + HepG2 1 ng/ul   1.0E2
DNA Template                 —      —      1  PSP65 HBV + HepG2 1 ng/ul   1.0E1

Total:   10 H2O
```

Figure 22:
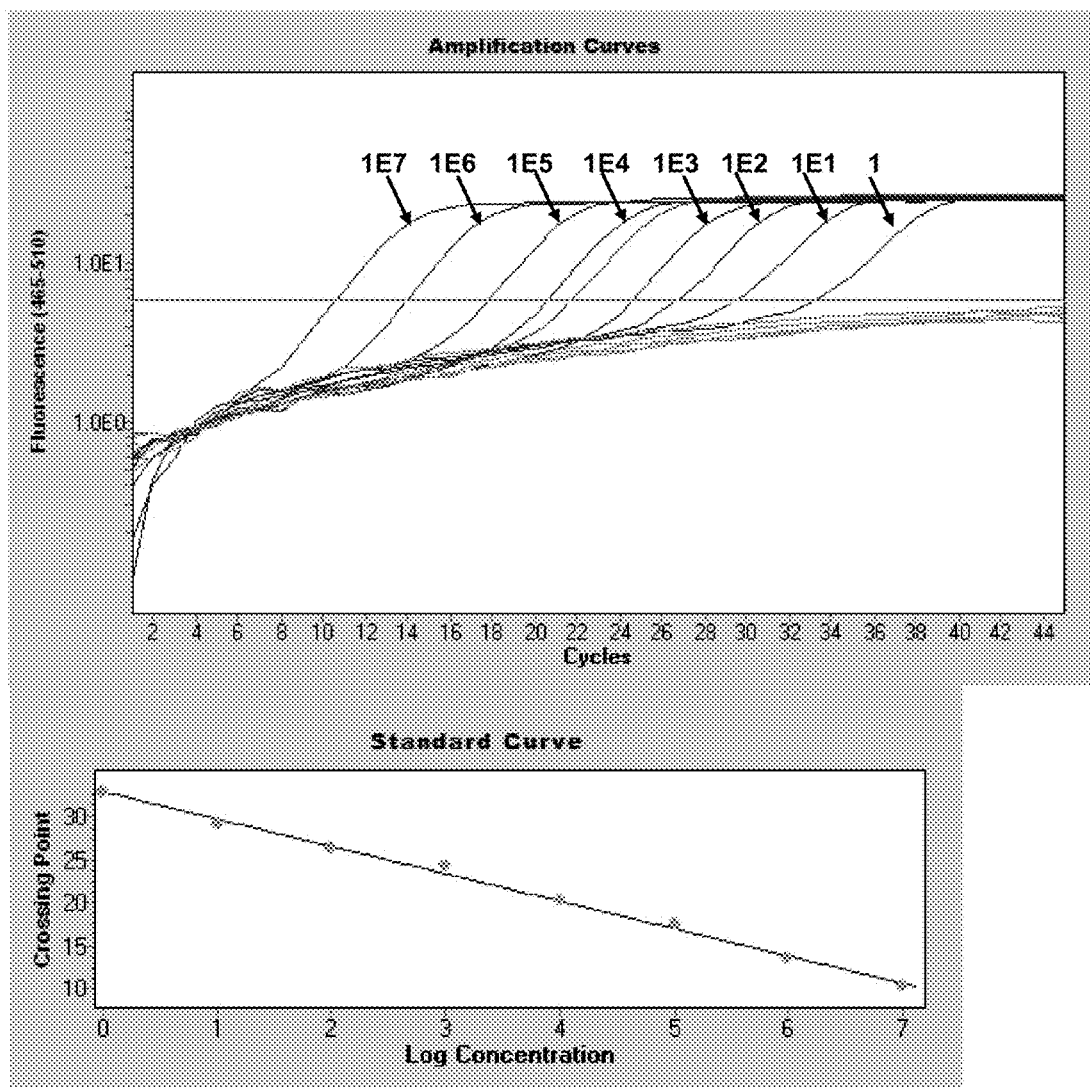
FIG. 22 shows results using the protocol for quantification of genomic CpG island 3 of the HBV genome.

Below is the detailed protocol for quantification of genomic CpG island 3 of the HBV genome (results shows in FIG. 22).

```
                                                                  Product
Primer/Probe                    Sequence: 5' to 3'                Size HBV gp4 Fwd3a1 (SEQ ID NO: 38)  TACAGACCACCAAATGCC               54 bp HBV gp4 Rev3a (SEQ ID NO: 39)   AACAACAGTAGTTTCCGGAAGTGTTGA HBV gp4 Probe_53bp (SEQ ID NO: 40) [6FAM] C+CTAT+C+T+TA T+CAA+CA+CTT+C
                                   [BHQ1]
```

```
"+" indicates LNA nucleotide
Roche Light Cycler 480 - Template: Mono-color Hydrolysis Probe
95° C. 5 min, (95° C. 10 s 65° C. 10 s, 72° C. 15 s) x 40 cycles
Component               [Stock]  [Final]  uL/rxn  DNA Template            HBV Copy/ul LC480 Probe Master       2x      1x       5       PSP65 HBV + HepG2 1 ng/ul   1.0E7
Mix                                                PSP65 HBV + HepG2 1 ng/ul   1.0E6
HBV240F3/C240R1          10 uM   1 uM     1       PSP65 HBV + HepG2 1 ng/ul   1.0E5
Probe (HBV240            2 uM    0.15 uM  .75     PSP65 HBV + HepG2 1 ng/ul   1.0E4
TaqMan)                                            PSP65 HBV + HepG2 1 ng/ul   1.0E3
H2O                      —       —        2.25    PSP65 HBV + HepG2 1 ng/ul   1.0E2
DNA Template             —       —        1       PSP65 HBV + HepG2 1 ng/ul   1.0E1

Total:   10      PSP65 HBV + HepG2 1 ng/ul   1.0
                                                   HepG2 1 ng/ul
                                                   H2O
```

All references cited in this application are incorporated by reference into this application in their entireties.

REFERENCES CITED

Chan, K. C. A., Lai, P. B. S., Mok, T. S. K., Chan, H. L. Y., Ding, C., Yeung, S. W., & Lo, Y. M. D. (2008). Quantitative Analysis of Circulating Methylated DNA as a Biomarker for Hepatocellular Carcinoma. *Clinical Chemistry,* 54(9), 1528-1536.

Diehl, F., Schmidt, K., Choti, M. A., Romans, K., Goodman, S., Li, M., . . . Diaz Jr, L. A. (2008). Circulating mutant DNA to assess tumor dynamics. *Nat Med,* 14(9), 985-990.

El-Serag, H. B., & Mason, A. C. (1999). Rising incidence of hepatocellular carcinoma in the United States. *New Engl J Med,* 340, 745-750.

Forshew, T., Murtaza, M., Parkinson, C., Gale, D., Tsui, D. W. Y., Kaper, F., . . . Rosenfeld, N. (2012). Noninvasive Identification and Monitoring of Cancer Mutations by Targeted Deep Sequencing of Plasma DNA. *Science Translational Medicine,* 4(136), 136ra168. doi: 10.1126/scitranslmed.3003726

Guo, Y., Li, Y., Mu, S., Zhang, J., & Yan, Z. (2009). Evidence that methylation of hepatitis B virus covalently closed circular DNA in liver tissues of patients with chronic hepatitis B modulates HBV replication. *Journal of Medical Virology,* 81(7), 1177-1183. doi: 10.1002/jmv.21525

Jain S, Chang T. T., Chen S. T., Boldbaatar B, Clemens A., Lin S. Y., Yan R., Hu C. T., Guo H. T., Block T. M., Song W. & Su Y. H. (2015). Comprehensive DNA methylation analysis of hepatitis B virus genome in infected liver tissues. Nature Scientific Reports |5:10478| DOI: 10.1038/srep 10478

Kaur, P., Paliwal, A., Durantel, D., Hainaut, P., Scoazec, J.-Y., Zoulim, F., . . . Herceg, Z. (2010). DNA Methylation of Hepatitis B Virus (HBV) Genome Associated with the Development of Hepatocellular Carcinoma and Occult HBV Infection. *Journal of Infectious Diseases,* 202(5), 700-704. doi: 10.1086/655398

Kim, J. W., Lee, S. H., Park, Y. S., Hwang, J. H., Jeong, S. H., Kim, N., & Lee, D. H. (2011). Replicative Activity of Hepatitis B Virus Is Negatively Associated with Methylation of Covalently Closed Circular DNA in Advanced Hepatitis B Virus Infection. *Intervirology,* 54(6), 316-325.

Kirk, G. D., Lesi, O. A., Mendy, M., Szymanska, K., Whittle, H., Goedert, J. J., . . . Montesano, R. (2005). 249ser TP53 mutation in plasma DNA, hepatitis B viral infection, and risk of hepatocellular carcinoma. *Oncogene,* 24(38), 5858-5867.

Klintmalm, G. B. (1998). Liver transplantation for hepatocellular carcinoma: a registry report of the impact of tumor characteristics on outcome. *Annals of Surgery,* 228(4), 479-490.

Lleonart, M. E., Kirk, G. D., Villar, S., Lesi, 0. A., Dasgupta, A., Goedert, J. J., . . . Friesen, M. D. (2005). Quantitative analysis of plasma TP53 249Ser-mutated DNA by electrospray ionization mass spectrometry. *Cancer Epidemiology, Biomarkers and Prevention,* 14(12), 2956-2962.

Moolla, N., Kew, M., & Arbuthnot, P. (2002). Regulatory elements of hepatitis B virus transcription. *Journal of Viral Hepatitis,* 9(5), 323-331. doi: 10.1046/j.1365-2893.2002.00381.x Pathak, A. K., Bhutani, M., Kumar, S., Mohan, A., & Guleria, R. (2006). Circulating cell-free DNA in plasma/serum of lung cancer patients as a potential screening and prognostic tool. *Clinical Chemistry,* 52(10), 1833-1842.

Stroun, M., Anker, P., Lyautey, J., Lederrey, C., & Maurice, P. A. (1987). Isolation and characterization of DNA from the plasma of cancer patients. *Eur. J. Cancer & Clin Oncol.,* 23, 707-712.

Stroun, M., Anker, P., Maurice, P., Lyautey, J., Lederrey, C., & Beljanski, M. (1989). Neoplastic characteristics of the DNA found in the plasma of cancer patients. *Oncology,* 46, 318-322.

Su, Y. H., Wang, M., Brenner, D. E., Ng, A., Melkonyan, H., Umansky, S., . . . Block, T. M. (2004). Human urine contains small, 150 to 250 nucleotide-sized, soluble DNA derived from the circulation and may be useful in the detection of colorectal cancer. *Journal of Molecular Diagnostics,* 6(2), 101-107.

Tsutsui, M., Iizuka, N., Moribe, T., Miura, T., Kimura, N., Tamatsukuri, S., . . . Oka, M. (2010). Methylated cyclin D2 gene circulating in the blood as a prognosis predictor of hepatocellular carcinoma. *Clinica Chimica Acta,* 411 (7-8), 516-520.

Utting, M., Werner, W., Dahse, R., Schubert, J., & Junker, K. (2002). Microsatellite Analysis of Free Tumor DNA in Urine, Serum, and Plasma of Patients: A Minimally Invasive Method for the Detection of Bladder Cancer. *Clinical Cancer Research,* 8, 35-40.

Vivekanandan, P., Thomas, D., & Torbenson, M. (2008). Hepatitis B viral DNA is methylated in liver tissues. *Journal of Viral Hepatitis,* 15(2), 103-107.

Wong, I. H. N., Zhang, J., Lai, P. B. S., Lau, W. Y., & Lo, Y. M. D. (2003). Quantitative analysis of tumor-derived methylated p16INK4a sequences in plasma, serum, and blood cells of hepatocellular carcinoma patients. *Clinical Cancer Research,* 9, 1047-1052.

Wu, T.-L., Zhang, D., Chia, J.-H., Tsao, K.-C., Sun, C.-F., & Wu, J. T. (2002). Cell-free DNA: measurement in various carcinomas and establishment of normal reference range. *Clinica Chimica Acta,* 321(1-2), 77-87.

Yen, L.-C., Yeh, Y.-S., Chen, C.-W., Wang, H.-M., Tsai, H.-L., Lu, C.-Y., . . . Wang, J.-Y. (2009). Detection of KRAS Oncogene in Peripheral Blood as a Predictor of the Response to Cetuximab Plus Chemotherapy in Patients with Metastatic Colorectal Cancer. *Clinical Cancer Research,* 15(13), 4508-4513. doi: 10.1158/1078-0432.ccr-08-3179

Zhang, X., Hou, J., & Lu, M. (2013). Regulation of Hepatitis B virus Replication by Epigenetic Mechanisms and MicroRNAs. [Mini Review]. *Frontiers in Genetics,* 4. doi: 10.3389/fgene.2013.00202

Zhang, Y., Li, C., Zhang, Y., Zhu, H., Kang, Y., Liu, H., . . . Zhang, J. (2013). Comparative Analysis of CpG Islands among HBV Genotypes. *PLoS ONE,* 8(2), e56711. doi: 10.1371/journal.pone.0056711

Ziegler, A., Zangemeister-Wittke, U., & Stahel, R. A. (2002). Circulating DNA: a new diagnostic gold mine? *Cancer Treatment Reviews,* 28, 255-271.

What is claimed is:

1. A method of detecting presence or absence of hepatitis B virus (HBV)-associated hepatocellular carcinoma (HCC) in a mammal, comprising:
   (i) isolating DNA from one or more body fluids or tissues from said mammal;
   (ii) quantifying a level of HBV DNA by a real-time quantitative PCR, quantifying bisulfite converted HBV DNA by bisulfite specific PCR and quantifying methylation level of one or more regions of HBV DNA with a quantitative methylation assay;
   (iii) comparing the methylation level of the one or more regions of HBV DNA with the methylation level of the one or more regions of HBV DNA in one or more control body fluids or tissues from mammals known not to have HCC; and
   (iv) detecting the presence or absence of HCC, with an elevated methylation level in the one or more regions of HBV DNA as compared to the methylation level in the one or more regions of HBV DNA in the one or more control body fluids or tissues indicating the presence of HCC, and absence of elevated methylation levels indicating the absence of HCC;
   wherein the one or more regions of HBV DNA consist of CpG island 3, of the HBV genome;
   wherein a forward primer, a reverse primer and a probe for the real-time quantitative PCR are nucleotide sequences of SEQ ID No. 38, SEQ ID No. 39 and SEQ ID No. 40, respectively;
   wherein a forward primer, a reverse primer and a probe for the BSP are nucleotide sequences of SEQ ID No. 12, SEQ ID No. 13, and SEQ No. 14, respectively;
   wherein the MSP is a two-step MSP comprising a first step MSP and a second step MSP, and the one or more of HBV DNA comprise CpG island 3, wherein:
   a forward primer, a reverse primer for the first step MSP are nucleotide sequences of SEQ ID No. 18 and SEQ ID No. 16, respectively; and a forward primer, a reverse primer for the second step MSP are nucleotide sequences of SEQ ID No. 19 and SEQ ID No. 20, respectively.

2. A method of detecting presence or absence of hepatitis B virus (HBV)-associated hepatocellular carcinoma (HCC) in a mammal, comprising:
- (i) isolating DNA from one or more body fluids or tissues from said mammal;
- (ii) quantifying a level of HBV DNA by a real-time quantitative PCR, quantifying bisulfite converted HBV DNA by bisulfite specific PCR and quantifying methylation level of one or more regions of HBV DNA with a quantitative methylation assay;
- (iii) comparing the methylation level of the one or more regions of HBV DNA with the methylation level of the one or more regions of HBV DNA in one or more control body fluids or tissues from mammals known not to have HCC; and
- (iv) detecting the presence or absence of HCC, with an elevated methylation level in the one or more regions of HEY DNA as compared to the methylation level in the one or more regions of HBV DNA in the one or more control body fluids or tissues indicating the presence of HCC, and absence of elevated methylation levels indicating the absence of HCC;

wherein the one or more regions of HBV DNA consists of CpG island 3 of the HBV genome;

wherein a forward primer, a reverse primer and a probe for the real-time quantitative PCR are nucleotide sequences of SEQ ID No. 38, SEQ ID No. 39 and SEQ ID No. 40, respectively, wherein a forward primer, a reverse primer and a probe for the BSP are nucleotide sequences of SEQ ID No. 12, SEQ ID No. 13, and SEQ No. 14, respectively;

wherein the MSP is a two-step MSP comprising a first step MSP and a second step MSP, and the one or more regions of HBV DNA consist of CpG island 3, wherein:
- a forward primer and a reverse primer for the first step MSP are nucleotide sequences of SEQ ID No. 21 and SEQ ID No. 22, respectively; and a forward primer, a reverse primer and a probe for the second step MSP are nucleotide sequences of SEQ ID No. 21, SEQ ID No. 23 and SEQ ID No. 24, respectively.

* * * * *

UNITED STATES PATENT AND TRADEMARK OFFICE
CERTIFICATE OF CORRECTION

PATENT NO. : 9,840,742 B2
APPLICATION NO. : 14/741442
DATED : December 12, 2017
INVENTOR(S) : Wei Song et al.

Page 1 of 1

It is certified that error appears in the above-identified patent and that said Letters Patent is hereby corrected as shown below:

In the Specification

Column 1, Line 15, replace "FUNDING" with --SUPPORT--;

Column 1, Lines 17-19, replace the whole paragraph, which reads "This invention was (made with government support under 2R44CA165312-02, awarded by the National Cancer Institute. The government has certain rights in the invention." with the paragraph --This invention was made with government support under R44CA165312 awarded by the National Institutes of Health. The government has certain rights in the invention.--.

Signed and Sealed this
Fifth Day of May, 2020

Andrei Iancu
*Director of the United States Patent and Trademark Office*

SEQUENCE LISTING

<160> NUMBER OF SEQ ID NOS: 40

<210> SEQ ID NO 1
<211> LENGTH: 24
<212> TYPE: DNA
<213> ORGANISM: Hepatitis B virus

<400> SEQUENCE: 1 ggttttttttt gttgataaga attt                                          24

<210> SEQ ID NO 2
<211> LENGTH: 22
<212> TYPE: DNA
<213> ORGANISM: Hepatitis B virus

<400> SEQUENCE: 2 cccctaaaa aattaaaaaa aa                                              22

<210> SEQ ID NO 3
<211> LENGTH: 33
<212> TYPE: DNA
<213> ORGANISM: Hepatitis B virus
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (25)..(25)
<223> OTHER INFORMATION: C or T
<220> FEATURE:
<221> NAME/KEY: misc_feature
<222> LOCATION: (33)..(33)
<223> OTHER INFORMATION: BHQ1

<400> SEQUENCE: 3
ttataatatt atagagttta gattygtggt gga                                 33

<210> SEQ ID NO 4
<211> LENGTH: 30
<212> TYPE: DNA
<213> ORGANISM: Hepatitis B virus

<400> SEQUENCE: 4
acgtgttttg gttaaaattc gtagttttta                                     30

<210> SEQ ID NO 5
<211> LENGTH: 27
<212> TYPE: DNA
<213> ORGANISM: Hepatitis B virus

<400> SEQUENCE: 5
aatataataa aacgccgcaa acacatc                                        27

<210> SEQ ID NO 6
<211> LENGTH: 32
<212> TYPE: DNA
<213> ORGANISM: Hepatitis B virus
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (32)..(32)
<223> OTHER INFORMATION: BHQ1

<400> SEQUENCE: 6 gtttttaat tgttttggt tatcgttgga tg                                32

<210> SEQ ID NO 7
<211> LENGTH: 25
<212> TYPE: DNA
<213> ORGANISM: Hepatitis B virus

<400> SEQUENCE: 7 ggattttgg atttttagta atgtt                                       25

<210> SEQ ID NO 8
<211> LENGTH: 26
<212> TYPE: DNA
<213> ORGANISM: Hepatitis B virus

<400> SEQUENCE: 8
ccaatcttta aacaaacaat ctttaa                                     26

<210> SEQ ID NO 9
<211> LENGTH: 32
<212> TYPE: DNA
<213> ORGANISM: Hepatitis B virus
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (8)..(8)
<223> OTHER INFORMATION: C or T
<220> FEATURE:
<221> NAME/KEY: misc_feature
<222> LOCATION: (12)..(12)
<223> OTHER INFORMATION: C or T
<220> FEATURE:
<221> NAME/KEY: misc_feature
<222> LOCATION: (32)..(32)
<223> OTHER INFORMATION: BHQ1

<400> SEQUENCE: 9
atgttaayga tygattttga ggtatatttt aa                              32

<210> SEQ ID NO 10
<211> LENGTH: 19
<212> TYPE: DNA
<213> ORGANISM: Hepatitis B virus

<400> SEQUENCE: 10
tgtcgtttcg gtcgattac                                             19

<210> SEQ ID NO 11
<211> LENGTH: 20
<212> TYPE: DNA
<213> ORGANISM: Hepatitis B virus

<400> SEQUENCE: 11
cacgatccga caaataaaaa                                            20

<210> SEQ ID NO 12
<211> LENGTH: 27
<212> TYPE: DNA
<213> ORGANISM: Hepatitis B virus

<400> SEQUENCE: 12
ttatgttaat gttaatatgg gtttaaa                                    27

-continued

```
<210> SEQ ID NO 13
<211> LENGTH: 22
<212> TYPE: DNA
<213> ORGANISM: Hepatitis B virus

<400> SEQUENCE: 13
ttctcttcca aaataaaac aa                                                    22

<210> SEQ ID NO 14
<211> LENGTH: 25
<212> TYPE: DNA
<213> ORGANISM: Hepatitis B virus
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (15)..(15)
<223> OTHER INFORMATION: LNA
<220> FEATURE:
<221> NAME/KEY: misc_feature
<222> LOCATION: (18)..(18)
<223> OTHER INFORMATION: LNA
<220> FEATURE:
<221> NAME/KEY: misc_feature
<222> LOCATION: (19)..(19)
<223> OTHER INFORMATION: LNA
<220> FEATURE:
<221> NAME/KEY: misc_feature
<222> LOCATION: (20)..(20)
<223> OTHER INFORMATION: LNA
<220> FEATURE:
<221> NAME/KEY: misc_feature
<222> LOCATION: (21)..(21)
<223> OTHER INFORMATION: LNA
<220> FEATURE:
<221> NAME/KEY: misc_feature
<222> LOCATION: (23)..(23)
<223> OTHER INFORMATION: LNA
<220> FEATURE:
<221> NAME/KEY: misc_feature
<222> LOCATION: (25)..(25)
<223> OTHER INFORMATION: LNA
<220> FEATURE:
<221> NAME/KEY: misc_feature
<222> LOCATION: (25)..(25)
<223> OTHER INFORMATION: BBQ

<400> SEQUENCE: 14
ttagataatt attgtggttt tatat                                                25

<210> SEQ ID NO 15
<211> LENGTH: 21
<212> TYPE: DNA
<213> ORGANISM: Hepatitis B virus

<400> SEQUENCE: 15
gtgtggattc gtattttttt c                                                    21

<210> SEQ ID NO 16
<211> LENGTH: 20
<212> TYPE: DNA
<213> ORGANISM: Hepatitis B virus

<400> SEQUENCE: 16
gacgattaaa accttcgtct                                                      20

<210> SEQ ID NO 17
<211> LENGTH: 26
```

<212> TYPE: DNA
<213> ORGANISM: Hepatitis B virus

<400> SEQUENCE: 17
aacctacctc gtcgtctaac aacaat                                        26

<210> SEQ ID NO 18
<211> LENGTH: 38
<212> TYPE: DNA
<213> ORGANISM: Hepatitis B virus

<400> SEQUENCE: 18
gctcttcgtg gtgtggtgaa gaagaatttt ttcgtttc                           38

<210> SEQ ID NO 19
<211> LENGTH: 17
<212> TYPE: DNA
<213> ORGANISM: Hepatitis B virus

<400> SEQUENCE: 19
tgtggtgaag aagaatt                                                  17

<210> SEQ ID NO 20
<211> LENGTH: 16
<212> TYPE: DNA
<213> ORGANISM: Hepatitis B virus

<400> SEQUENCE: 20
gacgattaaa accttc                                                   16

<210> SEQ ID NO 21
<211> LENGTH: 22
<212> TYPE: DNA
<213> ORGANISM: Hepatitis B virus

<400> SEQUENCE: 21
agaatttttt cgtttcgtag ac                                            22

<210> SEQ ID NO 22
<211> LENGTH: 26
<212> TYPE: DNA
<213> ORGANISM: Hepatitis B virus

<400> SEQUENCE: 22
aaaatcttct acgacgcgac gattaa                                        26

<210> SEQ ID NO 23
<211> LENGTH: 21
<212> TYPE: DNA
<213> ORGANISM: Hepatitis B virus

<400> SEQUENCE: 23
ctacgacgcg acgattaaaa c                                             21

<210> SEQ ID NO 24
<211> LENGTH: 19
<212> TYPE: DNA
<213> ORGANISM: Hepatitis B virus
<220> FEATURE:
<221> NAME/KEY: misc_feature
<222> LOCATION: (19)..(19)
<223> OTHER INFORMATION: phosphorylation modification

<400> SEQUENCE: 24

```
tcgtttcgta gacgaaggt                                             19

<210> SEQ ID NO 25
<211> LENGTH: 18
<212> TYPE: DNA
<213> ORGANISM: Hepatitis B virus

<400> SEQUENCE: 25
gtctagactc gtggtgga                                              18

<210> SEQ ID NO 26
<211> LENGTH: 15
<212> TYPE: DNA
<213> ORGANISM: Hepatitis B virus

<400> SEQUENCE: 26
ttttggccag gacac                                                 15

<210> SEQ ID NO 27
<211> LENGTH: 24
<212> TYPE: DNA
<213> ORGANISM: Hepatitis B virus
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (24)..(24)
<223> OTHER INFORMATION: BHQ1

<400> SEQUENCE: 27
caattttcta gggggagcac ccac                                       24

<210> SEQ ID NO 28
<211> LENGTH: 20
<212> TYPE: DNA
<213> ORGANISM: Hepatitis B virus

<400> SEQUENCE: 28
acttcgcttc acctctgcac                                            20

<210> SEQ ID NO 29
<211> LENGTH: 20
<212> TYPE: DNA
<213> ORGANISM: Hepatitis B virus

<400> SEQUENCE: 29
cacggtggtc tccatgctac                                            20

<210> SEQ ID NO 30
<211> LENGTH: 17
<212> TYPE: DNA
<213> ORGANISM: Hepatitis B virus

<400> SEQUENCE: 30
gaccaccgtg aacgccc                                               17

<210> SEQ ID NO 31
<211> LENGTH: 29
<212> TYPE: DNA
<213> ORGANISM: Hepatitis B virus

<400> SEQUENCE: 31
agtccaagag tcctgttgtg caagacctt                                  29
```

<210> SEQ ID NO 32
<211> LENGTH: 21
<212> TYPE: DNA
<213> ORGANISM: Hepatitis B virus

<400> SEQUENCE: 32
aggtcttgcc caaggtctta c                                              21

<210> SEQ ID NO 33
<211> LENGTH: 21
<212> TYPE: DNA
<213> ORGANISM: Hepatitis B virus

<400> SEQUENCE: 33
ttgctgagag tccaagagtc c                                              21

<210> SEQ ID NO 34
<211> LENGTH: 25
<212> TYPE: DNA
<213> ORGANISM: Hepatitis B virus

<400> SEQUENCE: 34
aacgaccgac cttgaggcat acttc                                          25

<210> SEQ ID NO 35
<211> LENGTH: 27
<212> TYPE: DNA
<213> ORGANISM: Hepatitis B virus

<400> SEQUENCE: 35
ctcctcccag tctttaaaca aacagtc                                        27

<210> SEQ ID NO 36
<211> LENGTH: 26
<212> TYPE: DNA
<213> ORGANISM: Hepatitis B virus
<220> FEATURE:
<221> NAME/KEY: misc_feature
<222> LOCATION: (2)..(2)
<223> OTHER INFORMATION: A or G

<400> SEQUENCE: 36
trggggagga gataaggtta aaggtc                                         26

<210> SEQ ID NO 37
<211> LENGTH: 23
<212> TYPE: DNA
<213> ORGANISM: Hepatitis B virus

<400> SEQUENCE: 37
atgcctacag cctcctagta caa                                            23

<210> SEQ ID NO 38
<211> LENGTH: 18
<212> TYPE: DNA
<213> ORGANISM: Hepatitis B virus

<400> SEQUENCE: 38
tacagaccac caaatgcc                                                  18

<210> SEQ ID NO 39
<211> LENGTH: 26
<212> TYPE: DNA

```
<213> ORGANISM: Hepatitis B virus

<400> SEQUENCE: 39
aacaacagta gtttccggaa gtgttg                                       26

<210> SEQ ID NO 40
<211> LENGTH: 19
<212> TYPE: DNA
<213> ORGANISM: Hepatitis B virus
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA
<220> FEATURE:
<221> NAME/KEY: misc_feature
<222> LOCATION: (16)..(16)
<223> OTHER INFORMATION: LNA
<220> FEATURE:
<221> NAME/KEY: misc_feature
<222> LOCATION: (19)..(19)
<223> OTHER INFORMATION: LNA
<220> FEATURE:
<221> NAME/KEY: misc_feature
<222> LOCATION: (19)..(19)
<223> OTHER INFORMATION: BHQ1

<400> SEQUENCE: 40
cctatcttat caacacttc                                               19
```